US008538113B2

(12) United States Patent
Tanaka et al.

(10) Patent No.: US 8,538,113 B2
(45) Date of Patent: Sep. 17, 2013

(54) IMAGE PROCESSING DEVICE AND METHOD FOR PROCESSING IMAGE TO DETECT LESION CANDIDATE REGION

(75) Inventors: Shino Tanaka, Tokyo (JP); Takashi Shirahata, Tokyo (JP); Takayuki Kadomura, Tokyo (JP); Hiroto Kokubun, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 295 days.

(21) Appl. No.: 13/060,506

(22) PCT Filed: Aug. 27, 2009

(86) PCT No.: PCT/JP2009/064958
§ 371 (c)(1),
(2), (4) Date: Feb. 24, 2011

(87) PCT Pub. No.: WO2010/024331
PCT Pub. Date: Mar. 4, 2010

(65) Prior Publication Data
US 2011/0164064 A1  Jul. 7, 2011

(30) Foreign Application Priority Data

Sep. 1, 2008  (JP) ................................. 2008-222978

(51) Int. Cl.
*G06K 9/00*  (2006.01)
(52) U.S. Cl.
USPC ......................................................... 382/131

(58) Field of Classification Search
USPC ..... 382/128–134; 128/920–925; 356/39–49; 600/407–414, 424–426; 345/581–618
See application file for complete search history.

(56) References Cited

U.S. PATENT DOCUMENTS

| 2005/0152588 A1* | 7/2005 | Yoshida et al. ............... 382/128 |
| 2005/0226483 A1* | 10/2005 | Geiger et al. ................. 382/128 |
| 2006/0115135 A1 | 6/2006 | Dehmeshki et al. |

FOREIGN PATENT DOCUMENTS

| JP | 2004-351056 | 12/2004 |
| JP | 2006-230910 | 9/2006 |
| WO | WO2006/056798 | 6/2006 |

OTHER PUBLICATIONS

International Search Report in PCT/JP2009/064958.
Nakazawa, Tetsuo, et al. (2008), "CT Colonoscopy no Kaihatsu," INNERVISION, vol. 23, No. 4, pp. 14-15.

* cited by examiner

*Primary Examiner* — Atiba O Fitzpatrick
(74) *Attorney, Agent, or Firm* — Cooper & Dunham LLP

(57) ABSTRACT

A medical image processing device is configured to set a parameter to be used for detecting a lesion candidate region. For example, the medical image processing device is configured to input a first parameter P1 estimating a dimension of the lesion, calculate a second parameter P2 based on the first parameter P1, calculate a feature amount indicating a shape of an organ surface by using the second parameter in the medical image, and extract the lesion candidate region based on the calculated feature amount.

12 Claims, 25 Drawing Sheets

| | MODE | VALUE | DISPLAY on/off |
|---|---|---|---|
| 1 | EARLY DETECTION | 6 | 1 |
| 2 | NORMAL | 10 | 0 |
| 3 | MANUAL | 8 | 0 |

FIG. 20
(a)
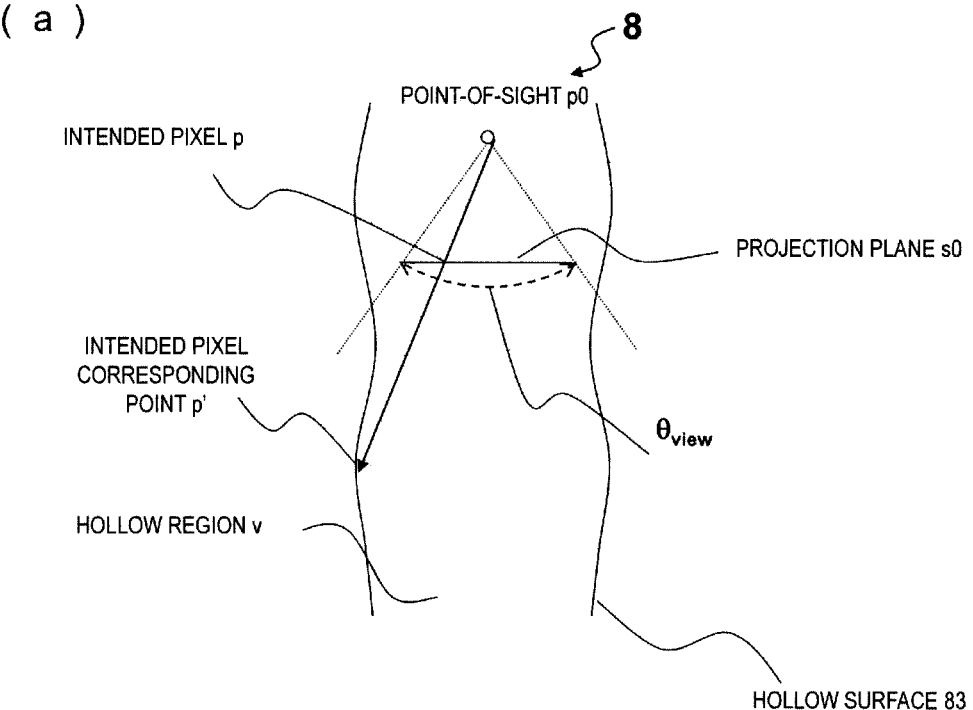
(b)
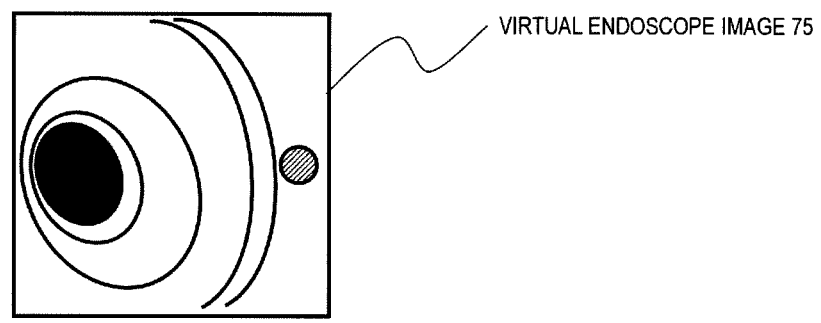

IMAGE PROCESSING DEVICE AND METHOD FOR PROCESSING IMAGE TO DETECT LESION CANDIDATE REGION

TECHNICAL FIELD

The present invention relates to an image processing device and the like for processing an image to be used for medical diagnostic purposes.

BACKGROUND ART

Tomographic images and the like of subjects, taken by a variety of devices such as the X-ray CT (computed tomography) machines and the MRI (magnetic resonance imaging) machines, have been conventionally known as images to be used for medical diagnostic purposes. Meanwhile, the computer-aided detections (hereinafter referred to as CADs) have been developed for: analyzing the aforementioned medical images with use of computers; detecting lesion candidates from shadows in the medical images; and providing a doctor with the detected lesion candidates. The CADs automatically detect regions expected as lesions in the images (hereinafter referred to as lesion candidate regions) based on shape properties and concentration properties of the lesions for reducing the burden of doctors.

For example, some of lesion candidates (e.g., polyps in regions of the large intestine) are formed in spherical shapes and thus have unique shape properties. In Patent Document 1, for instance, a curvature value typified by the shape index or the like is calculated as a feature amount indicating a shape property and abnormal shadow candidate regions are narrowed down based on the shape of a curved surface indicating concentration distribution of an image. In Patent Document 2, on the other hand, features indicating abnormality in a scanned image are highlighted and/or displayed comparably with the original scanned image as a user interface of a CAD for enhancing convenience of an operator.

Meanwhile, a technique has been developed for generating an image displaying the inside of a hollow organ developed about the axis of the hollow organ (hereinafter referred to as an panoramic image) as an image displaying method for actively diagnosing the insides of the hollow organs such as the large intestine (Patent Document 3). The panoramic images are advantageous in that doctors and the like can easily find lesion candidates because the entire surface of the hollow organ inside is viewable simultaneously. Further, a technique has been developed for generating a virtual endoscope image based on volume image data organized by the accumulation of plural sheets of tomographic images obtained by the aforementioned devices such as the X-ray CT devices (Patent Document 4). A virtual endoscope image is displayed by a method of: irradiating a projection object with a virtual ray from a virtual point-of-view set in the inside of a hollow organ; extracting a voxel with a brightness value greater than or equal to a predetermined threshold from voxels arranged on a line-of-sight; and projecting the extracted voxel on a projection surface. Similarly to an image obtained by an endoscope, the inside of an organ is observable with the virtual endoscope image (Patent Document 4).

PRIOR ART DOCUMENT

Patent Document
  Patent Document 1: JP-A-2006-230910
  Patent Document 2: JP-A-2008-512161
  Patent Document 3: Japanese Patent No. 3627066
  Patent Document 4: JP-A-7-296184

SUMMARY OF THE INVENTION

Problems that the Invention is to Solve

However, non-lesions such as the folds on the surface of an organ and/or lesions whose dimensions (e.g., polyp diameters) are extremely small are extracted when lesion candidate regions are extracted based on a curvature value as seen in the conventional CADs. Consequently, a drawback has been produced that lesion candidates cannot be narrowed down. Further, dimensions (e.g., polyp diameters) of lesions, intended to be detected by the CADs, depend on diagnostic purposes such as early detection of lesions and detection of advanced lesions. Various algorithms have been developed for extracting lesion candidate regions in accordance with features or the like of lesion tissues and polyps. The algorithms are lack of versatility although specialized in their respective purposes.

The invention is produced in view of the aforementioned drawbacks. It is an object of the invention to provide an image processing device and the like for detecting lesion regions under a condition that an operator is allowed to easily change detection objects in accordance with diagnostic purposes.

Means for Solving the Problems

To achieve the aforementioned object, a first aspect of the invention relates to an image processing device for detecting a lesion candidate region from a medical image. The image processing device is characterized to include: parameter setting means for setting a parameter to be used for detecting the lesion candidate region; and lesion candidate region detection means for assessing the medical image using the parameter set by the parameter setting means and detecting the lesion candidate region based on a result of the assessment.

Further, the image processing device preferably includes a data table that values of the parameter are preliminarily set in accordance with modes. The parameter setting means preferably includes first inputting means for reading out a value of the parameter corresponding to a selected mode from the data table and inputting the read-out value.

Further, the image processing device preferably includes second inputting means configured to input a numerical value as a value of the parameter. The parameter setting means preferably sets the numerical value input by the second inputting means as a value of the parameter.

The image processing device preferably includes third inputting means for displaying an object that a size or shape thereof varies in accordance with magnitude of a value of the parameter on a display screen displaying the medical image and inputting a value of the parameter through an operation with respect to the object. The parameter setting means preferably sets a value input by the third inputting means in accordance with the size or shape of the object as a value of the parameter.

The parameter setting means includes parameter inputting means configured to input a first parameter, and second parameter calculating means configured to calculate a second parameter based on the first parameter input by the parameter inputting means. The lesion candidate detecting means includes lesion candidate region extracting means and false positive deleting means. The lesion candidate region extracting means calculates a feature amount indicating the shape of an organ surface using the second parameter calculated by the second parameter calculating means with respect to the medical image and extracts the lesion candidate region based on the calculated feature amount. The false-positive deleting means determines a false-positive region by assessing a predetermined feature amount of the lesion candidate region extracted by the lesion candidate region extracting means and deletes the lesion candidate region when the lesion candidate region is determined as the false-positive region.

The second parameter is an inter-distance between differentiation reference points to be used in calculating a curvature value as the feature amount indicating the shape of the organ surface.

Further, the parameter setting means includes: parameter inputting means configured to input a first parameter; and third parameter calculating means configured to calculate a third parameter based on the first parameter input by the parameter inputting means. The lesion candidate detecting means includes lesion candidate region extracting means and false-positive deleting means. The lesion candidate region extracting means calculates a feature amount indicating the shape of the organ surface with respect to the medical image and extracts the lesion candidate region based on the calculated feature amount. The false-positive deleting means determines a false-positive region by assessing a predetermined feature amount of the lesion candidate region extracted by the lesion candidate region extracting means using the third parameter calculated by the third parameter calculating means and deletes the lesion candidate region when the lesion candidate region is determined as the false-positive region.

The third parameter includes at least either a parameter indicating the size of the lesion candidate region or a parameter indicating the shape of the lesion candidate region.

Further, the image processing device preferably further includes parameter correcting means for correcting the parameter set by the parameter setting means in accordance with deformation of the medical image. The lesion candidate region detecting means preferably assesses the medical image using the parameter corrected by the parameter correcting means and detects the lesion candidate region based on a result of the assessment.

The medical image is preferably an panoramic image displaying the inner surface of a hollow organ developed about an axis of the hollow organ.

The medical image is preferably a virtual endoscope image obtained by projecting the inside of a hollow organ on a predetermined projection plane from a virtual point-of-view set in the inside of the hollow organ.

A second aspect of the invention relates to an image processing method of detecting a lesion candidate region from a medical image. The image processing method is characterized to include: a parameter setting step of setting a parameter to be used for detecting the lesion candidate region; and a lesion candidate region detecting step of assessing the medical image using the parameter set in the parameter setting step and detecting the lesion candidate region based on a result of the assessment.

Advantage of the Invention

According to the invention, it is possible to provide an image processing device and the like for detecting lesion regions under a condition that an operator is allowed to easily change detection objects in accordance with diagnostic purposes.

BRIEF DESCRIPTION OF THE DRAWINGS

FIG. 12 is a diagram explaining a pathway radius.

FIG. 20 is a diagram explaining a virtual endoscope image.

MODE FOR CARRYING OUT THE INVENTION

Preferred exemplary embodiments of the invention will be hereinafter explained in detail with reference to attached figures.

(First Exemplary Embodiment)

First, the following explanation relates to the configuration of an image processing system 1 that an image processing device of the invention is applied.

Figure 1:
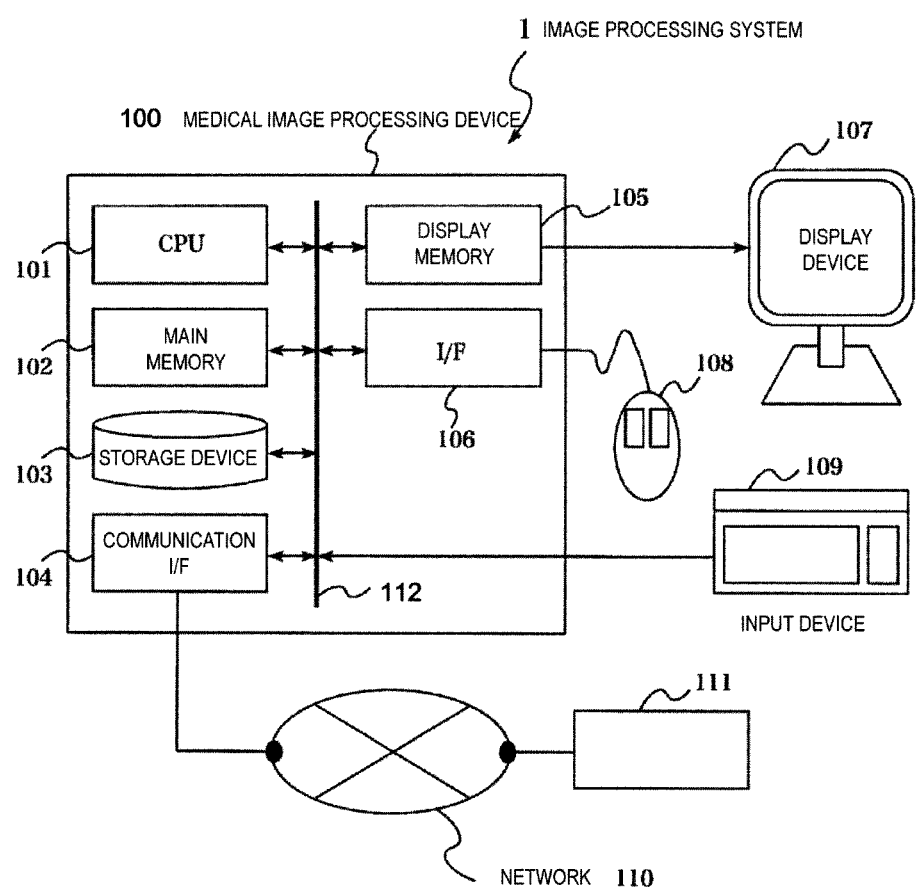
FIG. 1 is a hardware configuration diagram illustrating the entire configuration of an image processing system 1.

FIG. 1 is a hardware configuration diagram illustrating the entire configuration of the image processing system 1.

As illustrated in FIG. 1, the image processing system 1 includes a display device 107, a medical image processing device 100 equipped with an input device 109, and an image database 111 connected to the medical image processing device 100 through a network 110.

The medical image processing device 100 is a computer installed in a hospital or the like for image diagnostic purposes, and functions as a computer-aided detection (CAD) for analyzing a medical image, detecting lesion candidates from shadows in the medical image, and providing a doctor with the detected lesion candidates.

The medical image processing device 100 includes CPU (central processing unit) 101, a main memory 102, a storage device 103, a communication interface (communication I/F) 104, a display memory 105, and an interface (I/F) 106 with external devices such as a mouse 108. These components are respectively connected through a bus 112.

CPU 101 loads a program stored in the main memory 102, the storage device 103 or the like into a working memory area in RAM of the main memory 102, and executes the loaded program. Accordingly, drive controls are executed for the components connected through the bus 112 and the medical image processing device 100 is thereby allowed to implement various processing.

In the first exemplary embodiment, CPU 101 further executes a processing regarding legion candidate detection described below (see FIGS. 2 and 3).

The main memory 102 includes ROM (read only memory), RAM (random access memory) and the like. ROM permanently stores programs (e.g., a computer boot program and BIOS), data and the like. On the other hand, RAM temporarily stores programs, data and the like loaded from ROM, the storage device 103 and the like, and includes a working area to be used for allowing CPU 101 to execute various processing.

The storage device 103 is a storage device for reading/writing data from/to HDD (hard disc drive) and other storage media, and stores programs executed by CPU 101, data necessary for executing the programs, OS (operating system) and the like. A control program corresponding to OS and application programs are stored as the aforementioned programs. CPU 101 reads out respective program codes, transfers them to RAM of the main memory 102, and executes them as various means on an as-needed basis.

The communication I/F 104 includes a transmission control device, communication ports and the like, and mediates communication between the medical image processing device 100 and the network 110. Further, the communication I/F 104 controls the communication through the network 110 with the image database 111 and other computers or machines such as the X-ray CT machines or the MRI machines.

I/F 106 is a port for connecting peripheral devices to the medical image processing device 100, and data is transmitted/received to/from the peripheral devices through I/F 106. For example, an input device (e.g., the mouse 108) and the like may be connected to the medical image processing device 100 through I/F 106.

The display memory 105 is a buffer for temporarily storing display data to be input therein from CPU 101. The stored display data is output to the display device 107 at a predetermined timing.

The display device 107 includes a display unit (e.g., a liquid crystal panel or a CRT monitor) and a logic circuit for executing a display processing in cooperation with the display unit. The display device 107 is connected to CPU 101 through the display memory 105. The display device 107 displays the display data stored in the display memory 105 on the display unit in response to the control by CPU 101.

The input device 109 is, for instance, an input device such as a keyboard, and outputs to CPU 101 various commands and information to be input by an operator. An operator interactively operates the medical image processing device 100 using the external devices including the display device 107, the input device 109, the mouse 108 and the like.

The network 110 includes various communication networks such as LAN (local area network), WAN (wide area network), Intranet and Internet, and mediates the communication connections between the medical image processing device 100 and other components including the image database 111, a server, other information devices and the like.

The image database 111 accumulates and stores medical images taken by machines (the X-ray CT machines, the MRI machines, etc.) for taking images to be used for medical diagnostic purposes. For example, the image database 111 is installed in a server or the like of a hospital, a medical center or the like. In the image processing system 1 illustrated in FIG. 1, the image database 111 is designed to be connected to the medical image processing device 100 through the network 110. However, the image database 111 may be installed in the storage device 103, for instance, within the medical image processing device 100.

It is noted that the medical images, handled in the image processing system 1 of the invention, include tomographic images of subjects, panoramic images of the hollow organs, and virtual endoscope images. An panoramic image displays the inside of a hollow organ developed about the axis (pathway line) of the hollow organ (see FIG. 6). A virtual endoscope image displays the inside of a hollow organ from a virtual point-of-view set in the inside of the hollow organ with a display method based on perspective projection (see FIG. 20(*b*)).

Detection of lesion candidates in an panoramic image will be explained in the following first to third exemplary embodiments, whereas detection of lesion candidates in a virtual endoscope image will be explained in the following fourth exemplary embodiment.

Next, actions of the image processing system 1 will be explained with reference to FIGS. 2 to 8.

Figure 2:
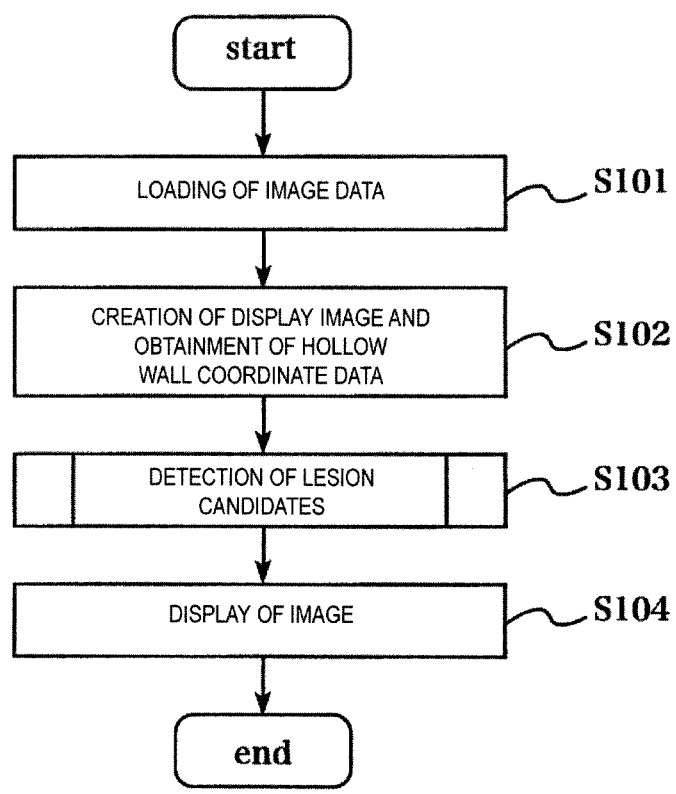
FIG. 2 is a flowchart representing the entire image processing flow to be executed in the image processing system 1.

FIG. 2 is a flowchart representing the entire flow of the image processing to be executed in the image processing system 1.

Figure 3:
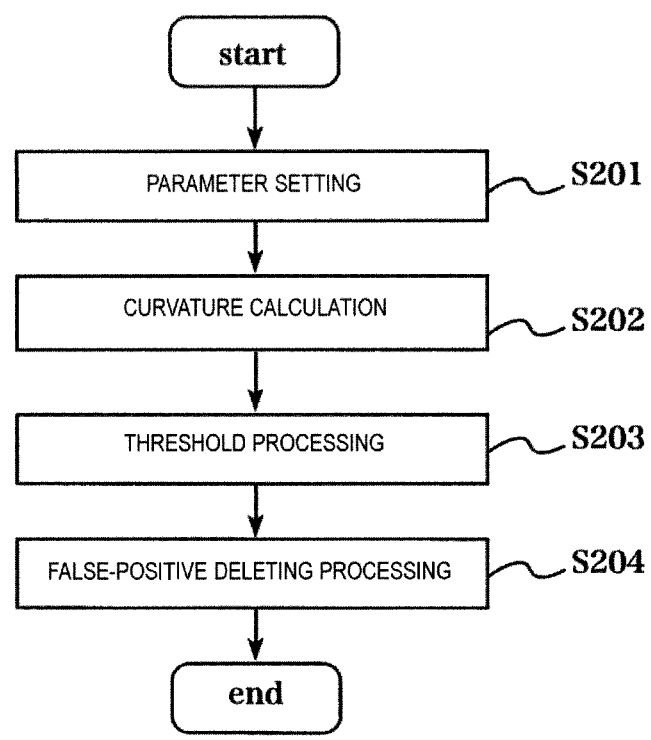
FIG. 3 is a flowchart explaining the flow of a processing regarding lesion candidate detection to be executed by a medical image processing device 100.

FIG. 3 is a flowchart explaining the flow of the processing regarding lesion candidate detection to be executed by the medical image processing device 100.

Figure 4:
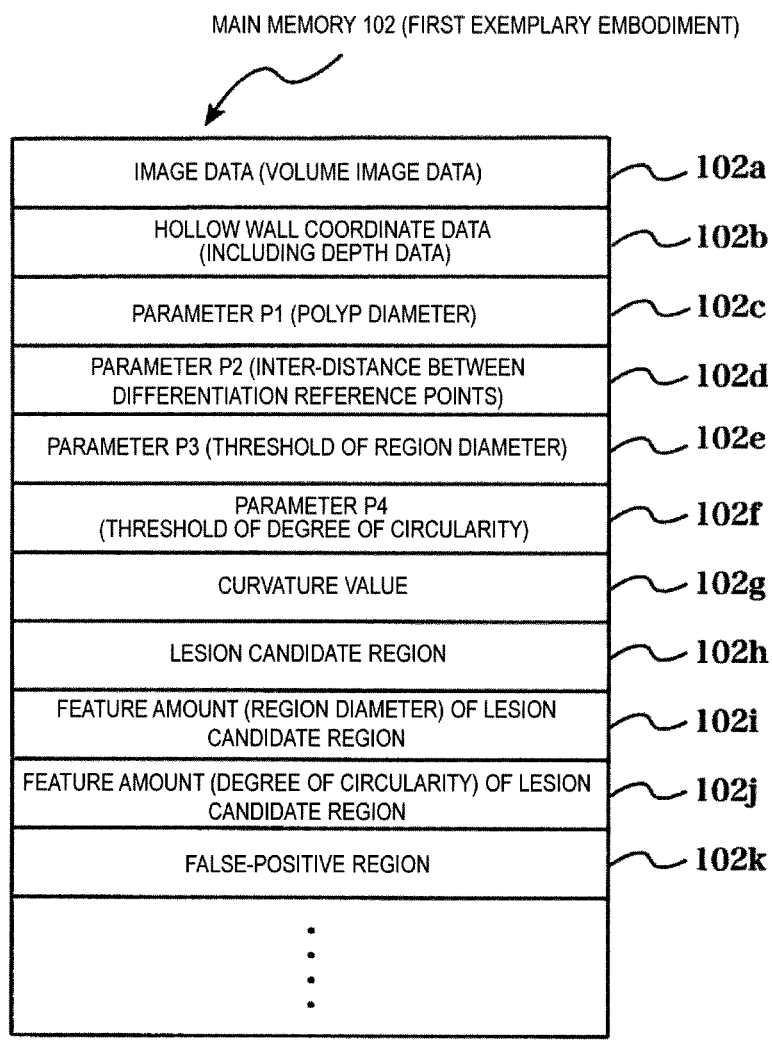
FIG. 4 is a data configuration diagram of a main memory 102 (first exemplary embodiment).

FIG. 4 is a diagram representing data to be stored in RAM of the main memory 102 in executing the image processing and the lesion candidate detection processing.

Figure 5:
FIG. 5 is an exemplary data table 2 that values of a parameter P1 are preliminarily set in accordance with modes.

FIG. 5 is a diagram representing an exemplary data table 2 that values of a parameter P1 are set in accordance with modes of the present exemplary embodiment.

Figure 6:
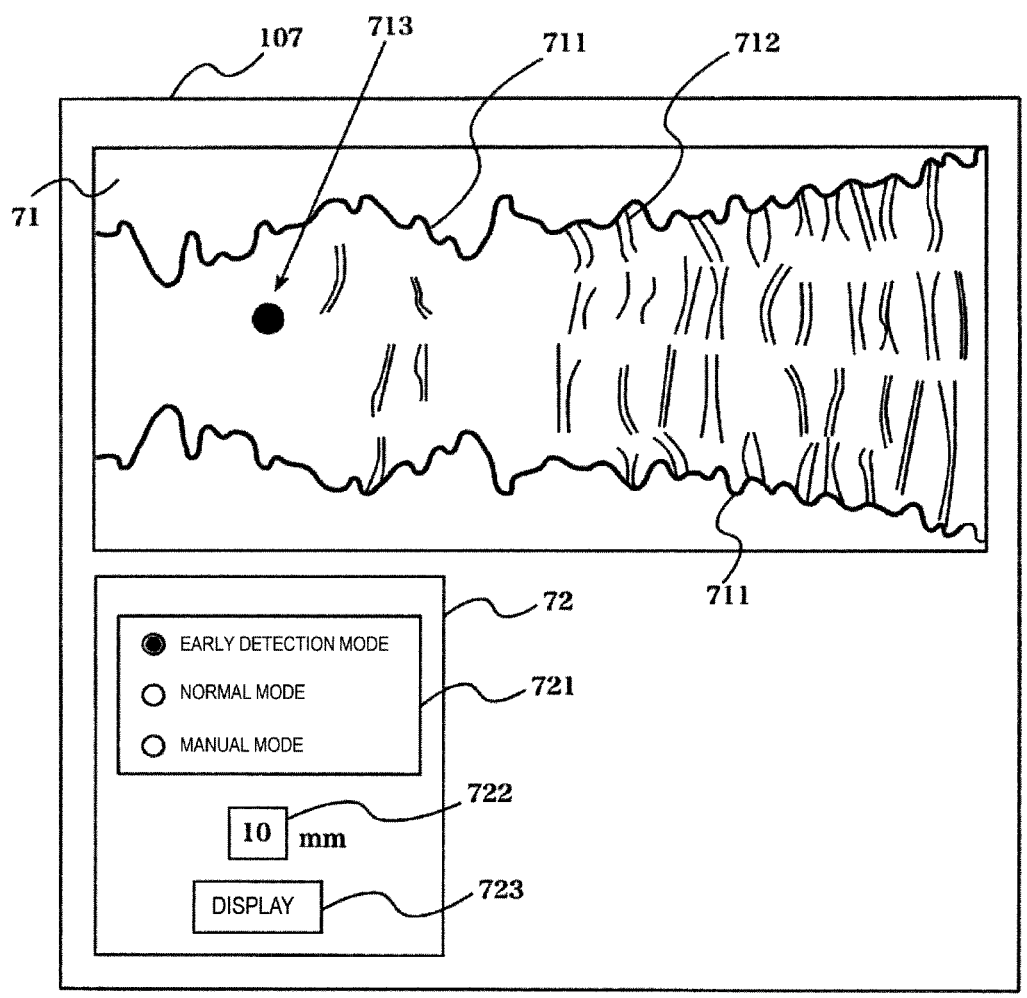
FIG. 6 illustrates a display example of an panoramic image 71 and a parameter setting window 72.

FIG. 6 is a display example of an panoramic image 71 and a parameter setting window 72.

Figure 7:
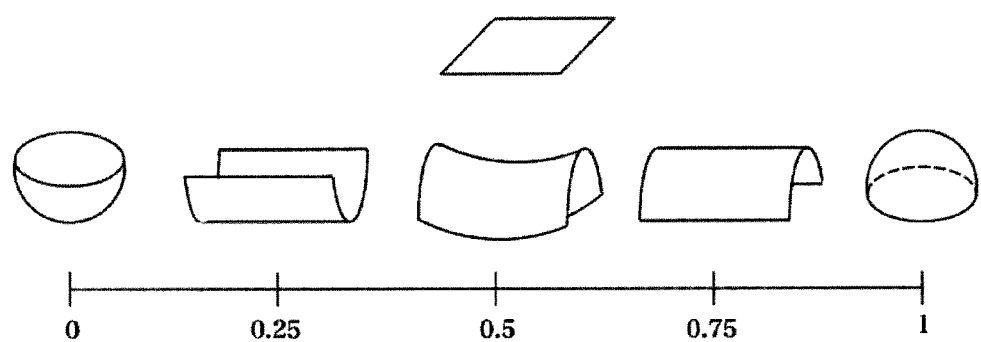
FIG. 7 is a diagram explaining the shape index.

FIG. 7 is a diagram explaining the shape index.

Figure 8:
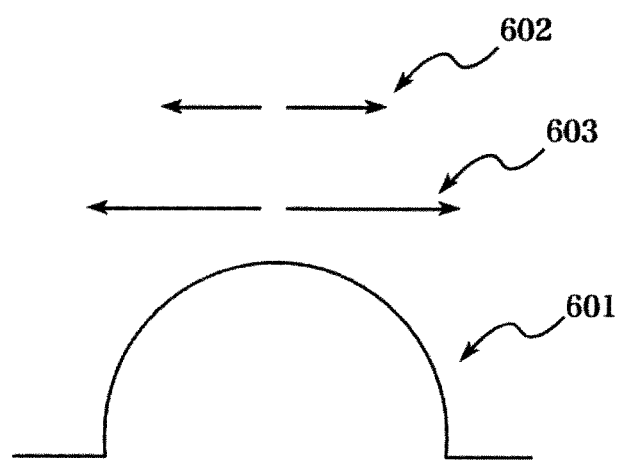
FIG. 8 is a diagram explaining inter-distance between differentiation reference points.

FIG. 8 is a diagram explaining inter-distance between differentiation reference points.

CPU 101 of the medical image processing device 100 reads out programs and data related to an image processing and a lesion candidate detection processing from the main memory 102 and executes the image processing and the lesion candidate detection processing based on the read-out programs and data.

At the onset of executing the image processing to be described, it is assumed that the image data has been already downloaded from the image database 111 or the like through the network 110 and the communication I/F 104 and stored in the storage device 103 of the medical image processing device 100.

In the image processing of FIG. 2, CPU 101 of the medical image processing device 100 firstly executes a processing of downloading image data. CPU 101 causes the display device 107 to display an image selection window displaying plural images to be selected in a list format or a thumbnail format, and receive a selection of an image from an operator. When an operator selects an intended image, CPU 101 reads out the corresponding image data of the selected image from the storage device 103 and keeps in the main memory 102 (Step S101, 102a in FIG. 4).

In the present exemplary embodiment, the image data of a hollow region is assumed to be selected. Further, the image data 102a to be loaded in this phase is assumed to be volume image data organized by the accumulation of plural tomographic images.

Next, CPU 101 creates a display image from the image data 102a loaded in Step S101. An panoramic image is herein assumed to be created as the display image. CPU 101 obtains hollow wall coordinate data 102b from the image data 102a. The hollow wall coordinate data 102b includes a real-space coordinate (x, y) corresponding to each point (each pixel) on a hollow wall displayed as the panoramic image, and a distance f (x, y) from a point on the hollow surface corresponding to the coordinate to a line passing through roughly the hollow center (hereinafter referred to as a pathway line) in the three-dimensional coordinate. The distance f (x, y) is referred to as "depth data" that is created by CPU 101 in creating an panoramic image. CPU 101 keeps the obtained hollow wall coordinate data 102b in the main memory 102 (Step S102, 102b in FIG. 4).

It is noted that creation of an panoramic image is disclosed in the aforementioned Patent Document 3 (Publication of Japan Patent No. 3627066) and explanation thereof will be hereinafter omitted.

Next, CPU 101 detects lesion candidates based on the hollow wall coordinate data 102b obtained in Step S102 (Step S103; continued to the lesion candidate detection processing in FIG. 3).

In the lesion candidate detection processing of FIG. 3, CPU 101 firstly sets a parameter to be used for the processing of detecting lesion candidates (Step S201). The parameter, set in Step S201, is referred to as "the parameter P1".

Values indicating dimension such as length (polyp diameter), area, volume and the like of a lesion can be assumed as the parameter P1. In the present exemplary embodiment, a value indicating the length (polyp diameter) of a lesion (e.g., polyp) as a detection object is set as the parameter P1, for instance.

The parameter P1 is also used for calculating a parameter P2 (inter-distance between differentiation reference points) to be used for calculating a curvature in Step S202, a parameter P3 (a threshold of a region diameter) to be used for a false-positive deleting processing in Step S204, and a parameter P4 (a threshold of a degree of circularity).

The aforementioned parameter P2, representing % inter-distance between differentiation reference points, is obtained by the following equation (1).

$$P2 = A \times P1 \tag{1}$$

Further, the aforementioned parameter P3, representing a threshold of a diameter (region diameter) of an extracted lesion candidate region, is expressed by the following equation (2).

$$P3 = B \times P1 \tag{2}$$

Yet further, the aforementioned parameter P4, representing a threshold of a degree of circularity of an extracted lesion candidate region, is expressed by the following equation (3).

$$P4 = C/P1 \tag{3}$$

In the above equations, A, B and C are constants.

In the parameter setting of Step S201, CPU 101 may be configured to read out one of the values preliminarily set in accordance with modes from the data table 2 of FIG. 5. Alternatively, an operator may be allowed to input a given numerical value through the input device 109.

Further alternatively, an object (e.g., a polyp image) may be displayed on the panoramic image created in the aforementioned Step S102, and the magnitude of the parameter P1 may be input by manipulating the size or shape of the object through an input operation using a pointing device (e.g., the mouse 108) and/or the input device 109. In this case, CPU 101 sets a value corresponding to the size (diameter) or shape expressed by the object as the parameter P1 and keeps the set value in the parameter P1 (102c in FIG. 4) of the main memory.

In the data table 2 represented in FIG. 5, for example, different default values have been preliminarily set for the respective modes as follows: "6" for an "early detection" mode; "10" for a "normal" mode; and "8" for a "manual" mode. In the data table 2, "display on/off" represents "on/off" of a mode change switch where "1" represents an "on" state and "0" represents an "off" state.

FIG. 6 illustrates a situation that the panoramic image 71 is displayed on the upper part of the display screen of the display device 107 while the parameter setting window 72 is displayed on the lower part of the display screen. In actual situations, shadows of the organ surface are displayed by grayscale (concentration information) in the panoramic image 71. In FIG. 6, however, the organ surface is expressed with solid lines for clearly expressing the drawing. Simply put, a region vertically interposed between two lines 711 corresponds to the inside surface of a hollow organ whereas plural vertical lines 712 depicted within the region correspond to folds of the organ surface.

In the parameter setting window 72 of FIG. 6, a mode list 721 of the selectable modes is displayed together with radio buttons, and a numerical value input box 722 for the parameter P1 is further displayed. Further, a "display" button 723 is pressed using the mouse 108 or the like after the parameter P1 is set. When an operator presses the "display" button 723 using the mouse 108 or the like, CPU 101 executes a lesion candidate detection processing (Steps S202 to S204) and lesion candidate regions are accordingly distinguishably displayed on the panoramic image 71.

In the example of FIG. 6, the "early detection" mode is being selected in the mode list 721 and "10" mm is further assumed to be input in the numerical value input box 722. When an operator inputs a value in the numerical value input box 722, the input value may be preferentially used even if a value of "6", preliminarily set for the "early detection" mode in the data table 2, is thus input as a default value. Subsequently, lesion candidates having a polyp diameter (the parameter P1) of roughly "10" mm are detected in the processing of Step S202 and thereafter to be described in response to the press of the display button 723, and the detected lesion candidates are accordingly distinguishably displayed as depicted with a marking 713.

After setting the parameter P1 as described above, CPU 101 calculates the parameters P2, P3 and P4 based on the parameter P1 using the aforementioned equations (1), (2) and (3) and keeps the calculated parameters in the main memory 102 (102d, 102e and 102f in FIG. 4).

When the parameters P1, P2, P3 and P4 are set in Step S201, CPU 101 calculates a first feature amount for each pixel p in the panoramic image 71 using the depth data f (x, y) of the panoramic image 71 (102b in FIG. 4). For example, the first feature amount is set as a curvature value. The curvature value is typified by the shape index, for instance (Step S202). CPU 101 keeps the calculated curvature value in the main memory 102 (102g in FIG. 4).

As represented in FIG. 7, the shape index is expressed by continuously varying values ranging from 0 to 1. The respective values correspond to different curved surface states. Simply put, a concave hemisphere corresponds to a shape index value of "0". A concave half-column, a saddle-shaped surface and a plane; a convex half-column, and a convex hemisphere are sequentially expressed in proportion to increase in a shape index value from "0". The convex hemisphere corresponds to a shape index value of "1".

The shape index is calculated by the following equation (4).

$$\text{Shape Index} = \frac{1}{2} - \frac{1}{\pi}\arctan\left(\frac{\lambda_{max} + \lambda_{min}}{\lambda_{max} - \lambda_{min}}\right) \quad (4)$$

In the above equation, $\lambda_{max}$ is a maximum value of a principle curvature for each point on a curved surface, whereas $\lambda_{min}$ is a minimum value of the principle curvature for each point on the curved surface.

The maximum value $\lambda_{max}$ and the minimum value $\lambda_{min}$ of the principle curvature are calculated by the following equations (5).

$$\left.\begin{array}{l}\lambda_{max} \equiv \frac{1}{2}\left[f_{xx} + f_{yy} + \sqrt{(f_{xx}+f_{yy})^2 - 4(f_{xx}f_{yy} - f_{xy}f_{xy})}\right]\\ \lambda_{min} \equiv \frac{1}{2}\left[f_{xx} + f_{yy} - \sqrt{(f_{xx}+f_{yy})^2 - 4(f_{xx}f_{yy} - f_{xy}f_{xy})}\right]\end{array}\right\} \quad (5)$$

In the above equations, $f_{xx}$, $f_{yy}$ and $f_{xy}$ are second-order partial derivatives of f (x, y) in an intended pixel p and are calculated by the following equations (6) using a coordinate (x, y) of the intended pixel p and the depth data f (x, y) in the intended pixel p.

$$\left.\begin{array}{l}f_{xx} = \dfrac{f(x+P2, y) + f(x-P2, y) - 2f(x,y)}{P2^2}\\ f_{yy} = \dfrac{f(x, y+P2) + f(x, y-P2) - 2f(x,y)}{P2^2}\\ f_{xy} = \dfrac{f(x+P2, y+P2) - f(x-P2, y+P2) - f(x+P2, y-P2) + f(x-P2, y-P2)}{P2^2}\end{array}\right\} \quad (6)$$

In the above equations, P2 is the inter-distance between differentiation reference points calculated in the aforementioned equation (1). The inter-distance between differentiation reference points refers to the distance between the intended pixel p and a pixel to be referred in calculating the second-order partial derivatives of the equations (6).

FIG. 8 is a diagram for explaining the inter-distance between differentiation reference points.

As an example, inter-distance P2 between differentiation reference points is herein set to be ½ of the parameter P1 (polyp diameter). Simply put, A is set to be ½ (i.e., A=½) in the aforementioned equation (1).

In calculating a curvature of a convex surface 601 illustrated in FIG. 8, a curvature value depends on the inter-distance between differentiation reference points. The curvature value is maximized when the inter-distance between differentiation reference points is roughly the same as the width of the curved surface (convex/concave). As depicted with arrows 602 in FIG. 8, a curvature is calculated for a substantially flat surface when the inter-distance between differentiation reference points is less than the width of the convex/concave. A shape index value of roughly 0.5 is herein obtained. On the other hand, a slope of the convex surface can be obtained in calculating the second-order partial derivatives when the inter-distance between differentiation reference points is roughly the same as the width of the convex/concave as depicted with arrows 603 in FIG. 8. Accordingly, a shape index value of roughly 1 is herein obtained, and this indicates that the convex surface is formed in an approximately convex hemispheric shape.

In the aforementioned example, ½ is set as the constant A (Equation (1)) to be used for calculating the inter-distance between differentiation reference points. However, the value of the constant A is not necessarily limited to the above.

Next, CPU 101 executes a threshold processing based on the calculated shape index (curvature value 102g) for each pixel p and extracts lesion candidate regions (Step S203). CPU 101 keeps the extracted lesion candidate regions in the main memory (a lesion candidate region 102h in FIG. 4).

The lesions (polyps) are formed in the shape of a convex curved surface. It is therefore herein assumed to preliminarily set the lower limit to the shape index, and CPU 101 determines a given pixel as a lesion candidate region when the pixel has a curvature value greater than or equal to the lower limit. For example, the lower limit is set to be 0.5.

Smaller curvature values are herein calculated in the case of a convex curved surface sized with a width extremely greater than the inter-distance between differentiation reference points. Therefore, such curvature values are exempted from lesion candidates and are not thereby extracted.

Next, CPU 101 calculates second and third feature amounts for each of the extracted lesion candidate regions (intended regions) and keeps the calculated feature amounts in the main memory 102 (a feature amount (region diameter) 102i and a feature amount (degree of circularity) 102j in FIG. 4). It is herein assumed that the second feature amount is a region diameter d of a lesion candidate region whereas the third feature amount is a degree-of-circularity k of a lesion candidate region. Next, CPU 101 executes the following assessment with respect to the second and third feature amounts of the respective intended regions. When a given intended region is determined to be a false-positive as a result of the determination, the intended region is deleted from the lesion candidate regions listed in Step S203 (Step S204).

When the region diameter d as the second feature amount is assessed in the false-positive deleting processing of Step S204, CPU 101 calculates the region diameter d of each lesion candidate region with reference to the coordinate data of each point on the hollow surface in the three dimensional real space. CPU 101 compares the calculated region diameter d (102i in FIG. 4) with the parameter P3 (equation (2); 102e in FIG. 4) set in Step S201. When the relation "d<P3" is established, CPU 101 determines that the intended region is a false-positive and deletes the intended region from the lesion candidate region 102h.

When the degree-of-circularity k as the third feature amount is assessed in the false-positive deleting processing of Step S204, CPU 101 calculates the degree-of-circularity k of each lesion candidate region with reference to the coordinate data of each point on the hollow surface in the three dimensional real space. CPU 101 compares the calculated degree-of-circularity k (102j in FIG. 4) with the parameter P4 (equation (3); 102f in FIG. 4) set in Step S201. When the relation "k<P4" is established, CPU 101 determines that the intended region is a false-positive (a false-positive region 102k in FIG. 4) and deletes the false-positive region 102k from the lesion candidate region 102h.

The region diameter d and the degree-of-circularity k are assessed as the feature amounts in the false-positive deleting processing of Step S204. However, the feature amounts are not limited to the above. For example, a horizontal-vertical ratio, a CT value and the like of an intended region may be set as the feature amounts, and a false-positive region may be determined based on the feature amounts.

Alternatively, the curvedness may be used as a feature amount to be used in the false-positive deleting processing of Step S204 and the like. The curvedness indicates the size of the curved surface. As to the convex surfaces, a large value of the curvedness indicates a small convex surface whereas a small value of the curvedness indicates a large convex surface. Therefore, the curvedness can be used as an indicator of a polyp diameter to be assessed. The curvedness is expressed by the following equation (7).

$$\text{curvedness} = \sqrt{\frac{\lambda_{max}^2 + \lambda_{min}^2}{2}} \quad (7)$$

When the curvedness is set as a feature amount, it is determined whether or not a given intended lesion candidate region is a false-positive by comparing average of the curvedness of the entire intended lesion candidate region with a predetermined value (a value proportional to inverse of the parameter P1). Further, an AND condition determination may be executed for the shape index and the curvedness in the threshold processing of Step S203.

The processing proceeds to Step S104 in FIG. 2 when the false-positive deleting processing of Step S204 is completed and a false-positive is accordingly deleted. CPU 101 distinguishably displays the lesion candidate regions on the panoramic image 71 using the markings 713 and the like (Step S104; see FIG. 6) and completes the image processing.

As explained above, the medical image processing device 100 in the image processing system 1 of the first exemplary embodiment executes a processing of detecting lesion candidate regions from an image of the organ surface. In the lesion candidate detection processing, the parameters to be used for detecting the lesion candidate regions are set in accordance with modes. Alternatively, an operator is allowed to set the parameter through the manual input of numerical values or through GUI. In the present exemplary embodiment, four types of parameters P1, P2, P3 and P4 are used, and the following settings are established: P1 as a polyp diameter; P2 as inter-distance between differentiation reference points; P3 as a threshold of a region diameter; and P4 as a threshold of a degree of circularity. CPU 101 calculates a shape-related feature amount (curvature value) of each point on the organ surface using a set parameter (P2) and determines a given point as a lesion candidate region when it corresponds to a predetermined shape.

Further, CPU 101 calculates the feature amounts such as a region diameter and a degree of circularity for the detected lesion candidate regions, determines whether or not the feature amounts correspond to the lesion candidates using the parameters (P3, P4), and deletes a given lesion candidate region when it is determined as a false-positive. Subsequently, CPU 101 distinguishably displays the lesion candidate regions on the image excluding the false-positive regions.

Thus, the parameters related to the detection of the lesion candidate regions are set in accordance with modes or are set by an operator. This makes it possible to detect lesion candidate regions under the condition that targets are easily changed in accordance with diagnostic purposes and to enhance versatility of CAD.

Further in the image processing system 1 of the present exemplary embodiment, the parameter to be used for calculating a curvature value (the inter-distance P2 between differentiation reference points) and the parameter to be used for assessing the feature amount in the false-positive deleting processing (the region diameter P3 and the degree-of-circularity P4) are calculated from the parameter (P1) firstly set by an operator. In other words, the single parameter P1 is secondarily used.

Thus, the parameters to be used for determining the other feature amounts (P2, P3 and P4) are calculated from the single set parameter (P1). Therefore, it is not necessary to separately input many parameters and this reduces complexity and effort of the parameter setting. Further, an operator is allowed to intuitively operate CAD easily when the parameter to be set by the operator is of a highly visible type indicating the size or shape of lesions (e.g., a polyp diameter). Yet further, operability will be enhanced when GUI is used for inputting the parameter.

In the present exemplary embodiment, the parameters P1 and P2 are set in association with each other where the parameter P1 is set as the length of a lesion and the parameter P2 is set as inter-distance between differentiation reference points. Accordingly, the lesion candidate region extracting processing can be executed using an appropriate value of the inter-distance between differentiation reference points in accordance with the length of a lesion candidate intended to be extracted, and it is possible to prevent a non-targeted lesion candidate from being extracted.

It is herein noted that the medical image exemplified in the first exemplary embodiment is an panoramic image of a hollow organ. However, the medical image is not limited to the above, and various medical images may be used including tomographic images, three dimensional volume images or the like of a subject. In such cases, the medical image processing device 100 is allowed to set the parameters related to the lesion candidate detection, and detects lesion candidates using the set parameters.

Further, the parameter of P1, amongst the parameters, is only configured to be input. However, parameters to be input are not limited to the parameter P1. For example, values preliminarily set in accordance with modes and operator's desired values may be input in the other parameters (P2, P3 and P4).

(Second Exemplary Embodiment)

Next, the image processing system 1 of a second exemplary embodiment will be explained. The hardware configuration of the image processing system 1 of the second exemplary embodiment is the same as the image processing system 1 of the first exemplary embodiment of FIG. 1. Therefore, explanation thereof will be hereinafter omitted, and a given component shared between the first and second exemplary embodiments will be explained while being given the same reference numeral.

In general, image deformation occurs in an panoramic image. It is therefore necessary to execute a processing in consideration of the image deformation for more accurately assessing the shape of the organ surface in detecting lesion candidates.

In the second exemplary embodiment, parameter correction is executed based on deformation of an panoramic image in setting parameters to be used for detecting lesion candidates.

The reasons of deformation of an panoramic image are assumed to be variation in pixel sizes (dy in FIG. 9), along a direction (y direction; hereinafter referred to as "a lateral direction") perpendicular to a longitudinal direction of the hollow organ with respect to each longitudinal (x directional) position of the panoramic image, curved of a hollow organ and the like. In other words, the circumference of a cross-section of a hollow organ in a given x position (longitudinal position) is assigned to pixels in the lateral direction at predetermined angular intervals in generating an panoramic image. However, circumferences of longitudinal cross-sections of an actual hollow organ are different from each other. Therefore, the pixel size dy varies and this results in deformation of an panoramic image.

Further, the distance between adjacent x positions (dx in FIG. 9) on the inside of a given curved region of a hollow organ is different from that on the outside of the curved region of the hollow organ. This results in image deformation.

Figure 10:
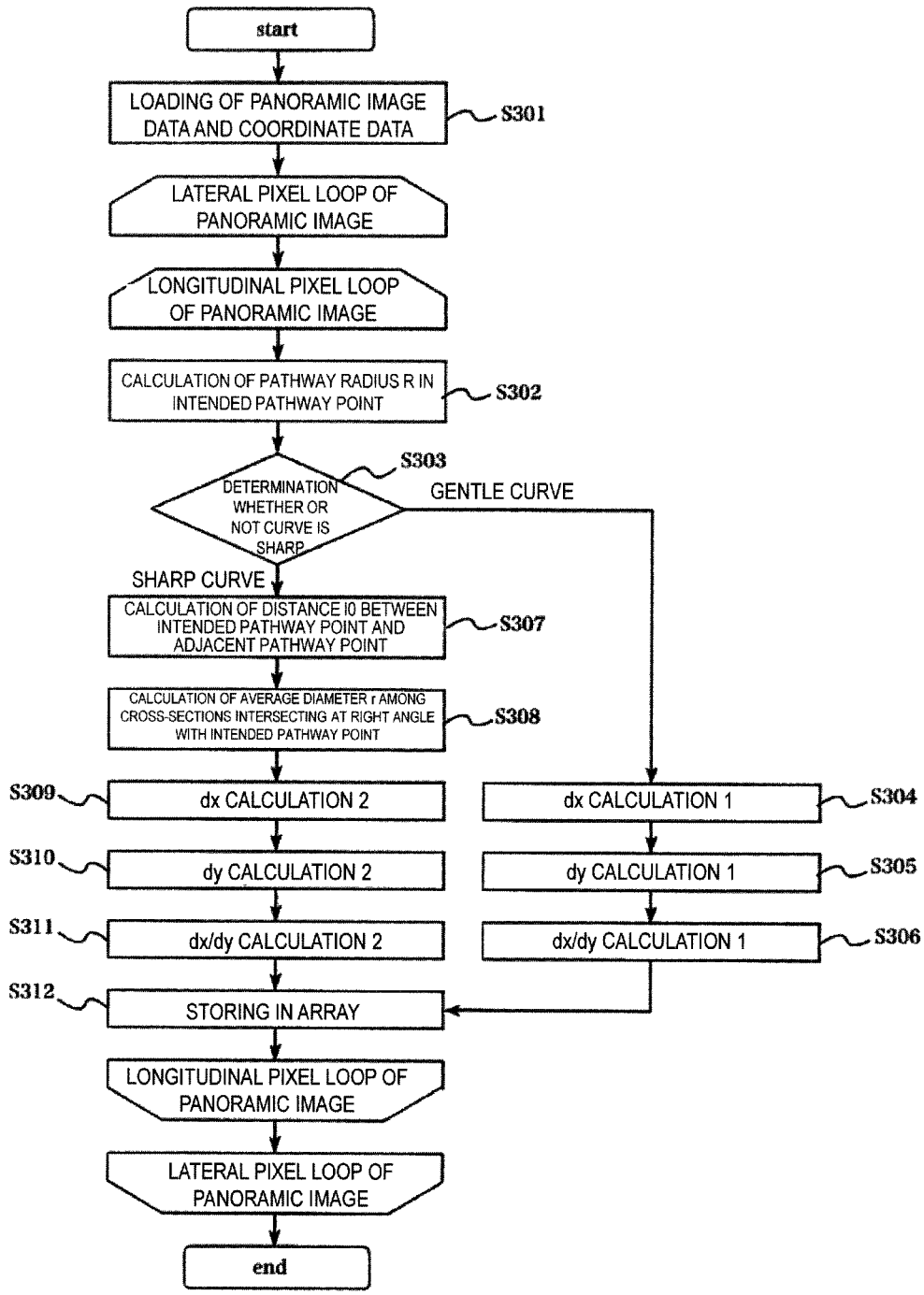
FIG. 10 is a flowchart explaining the flow of a pixel deformation calculation processing.

In view of the above, in the second exemplary embodiment, image deformation is calculated for each pixel by a pixel deformation calculation processing represented in FIG. 10 and calculates a deformation adjusted parameter (P2_x, P2_y) obtained by correcting the parameter P2 based on the calculated pixel deformation when the parameter setting processing of Step S201 is executed in the lesion candidate detection processing (see FIG. 3) of the first exemplary embodiment.

Figure 9:
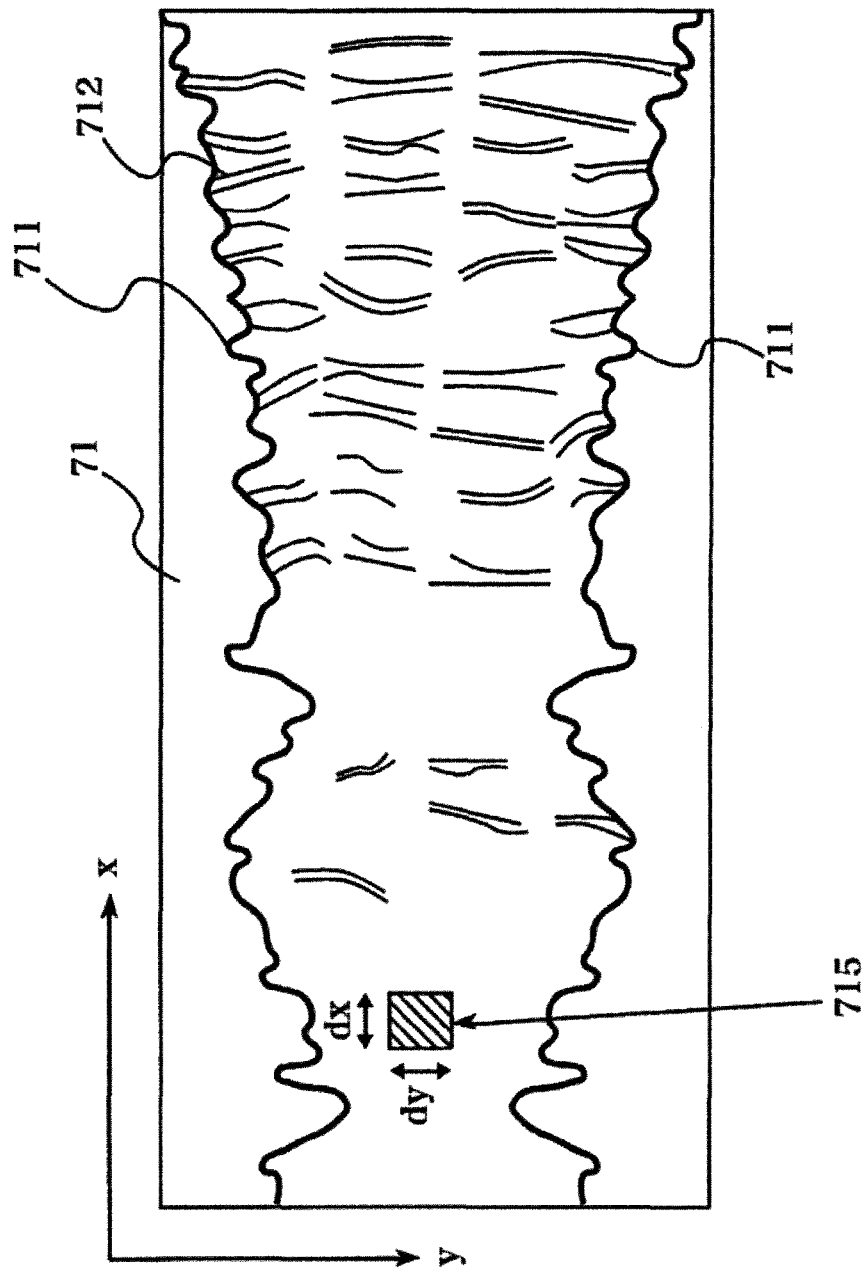
FIG. 9 is a diagram explaining directions of an panoramic image and directions of a pixel on the panoramic image.

FIG. 9 is a diagram for explaining the panoramic image 71 of a hollow organ and the directions of a given pixel on the panoramic image 71.

In the panoramic image 71 of FIG. 9, a longitudinal pathway line of the hollow organ is set as an x direction whereas a direction perpendicular to the pathway line (lateral direction) is set as a y direction. Further, the length of the actual organ surface, corresponding to an edge of a pixel 71s, is referred to as the pixel size. The x-directional pixel size will be hereinafter expressed as "dx" whereas the y-directional pixel size will be expressed as "dy". The pixel deformation is calculated as a ratio (dx/dy) between the x-directional pixel size and the y-direction pixel size in an intended pixel.

FIG. 10 is a flowchart explaining the flow of a pixel deformation calculation processing.

Figure 11:
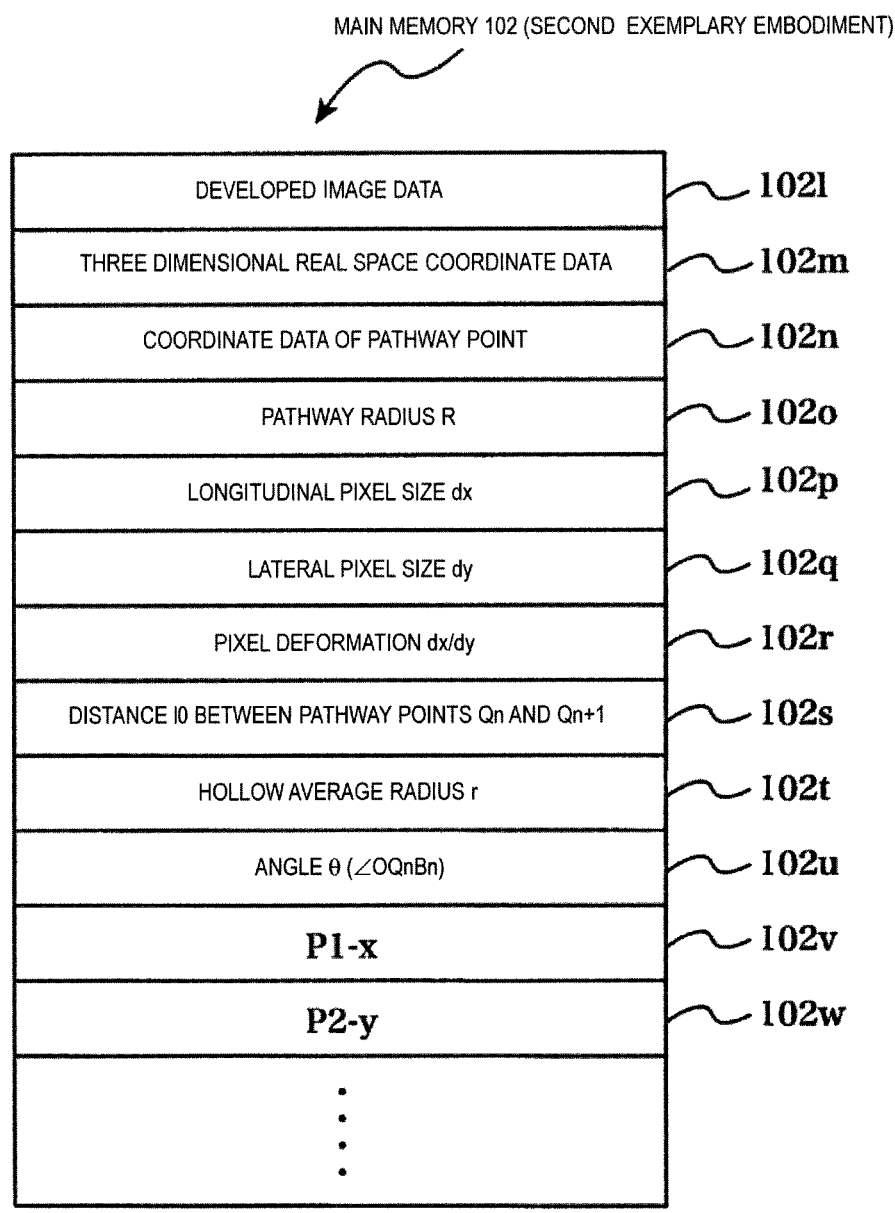
FIG. 11 is a data configuration diagram of the main memory 102 (second exemplary embodiment).
Figure 1:
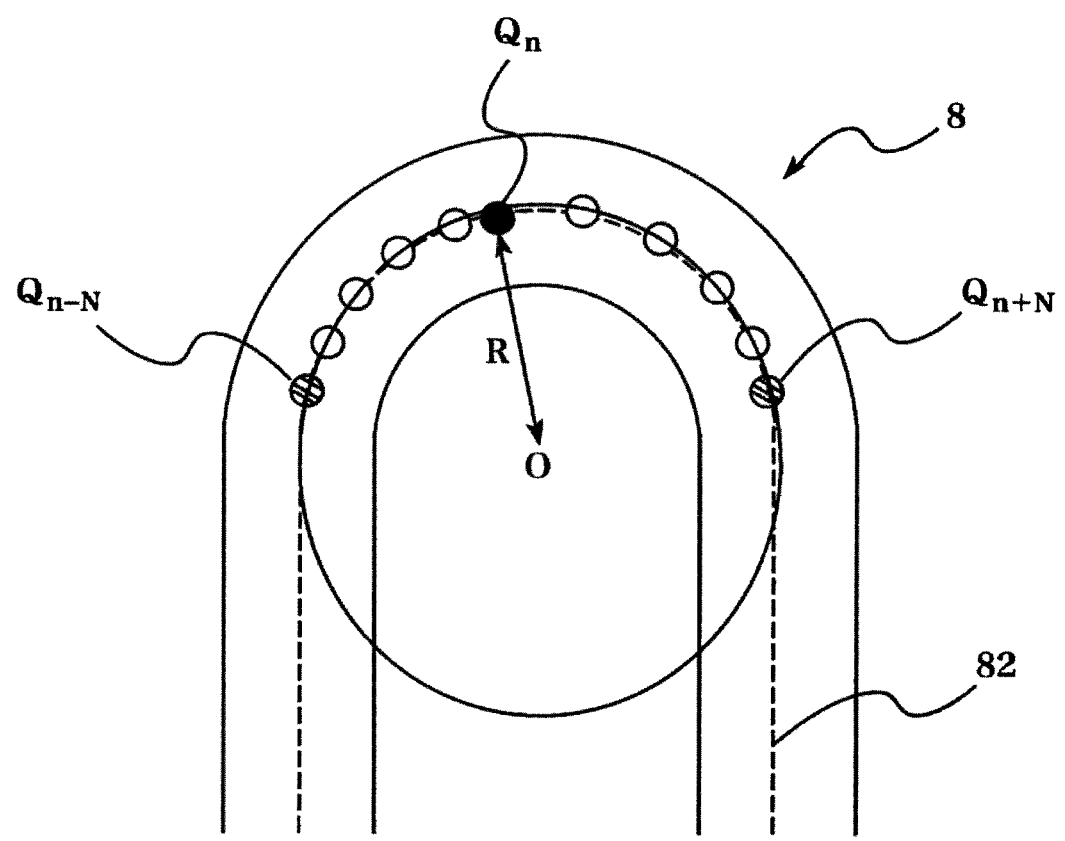

FIG. 11 is a diagram representing the data to be kept in RAM of the main memory 102 during execution of the pixel deformation calculation processing.

FIG. 12 is a diagram explaining a pathway radius R.

Figure 13:
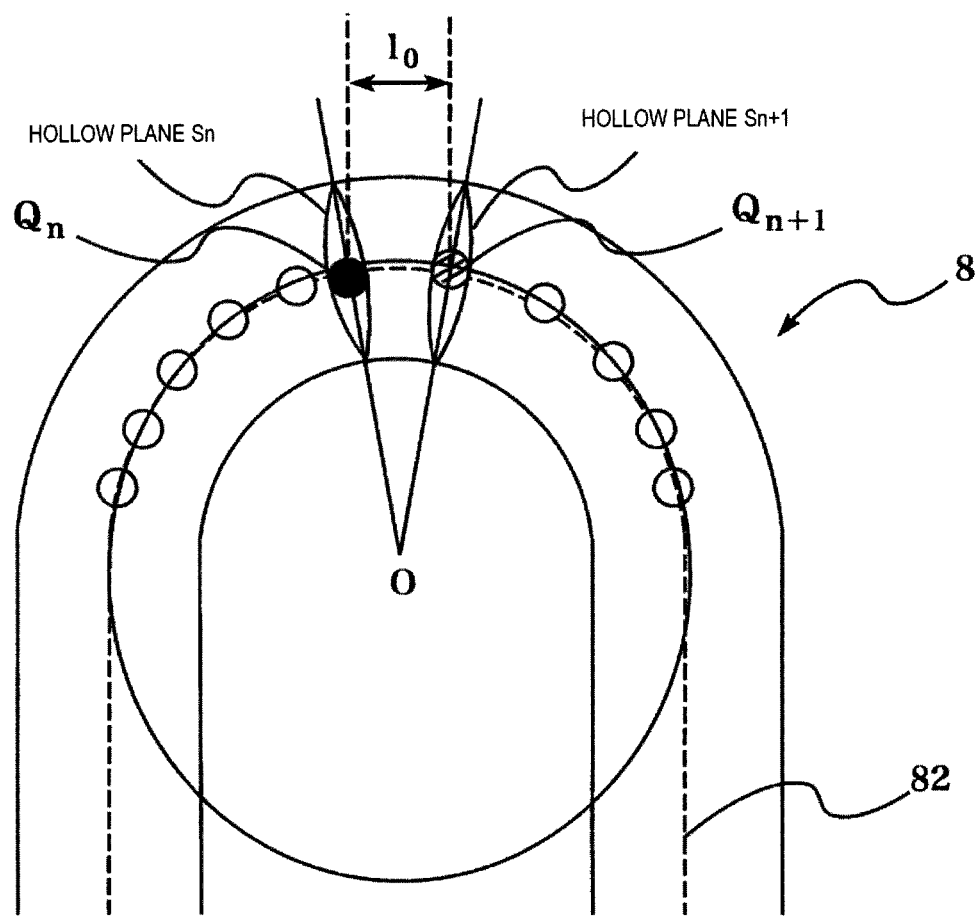
FIG. 13 is a diagram explaining distance between adjacent cross-sections.

FIG. 13 is a diagram explaining the distance between an intended cross-section (hollow plane $S_n$) and its adjacent cross-section (hollow plane $S_{n+1}$).

Figure 14:
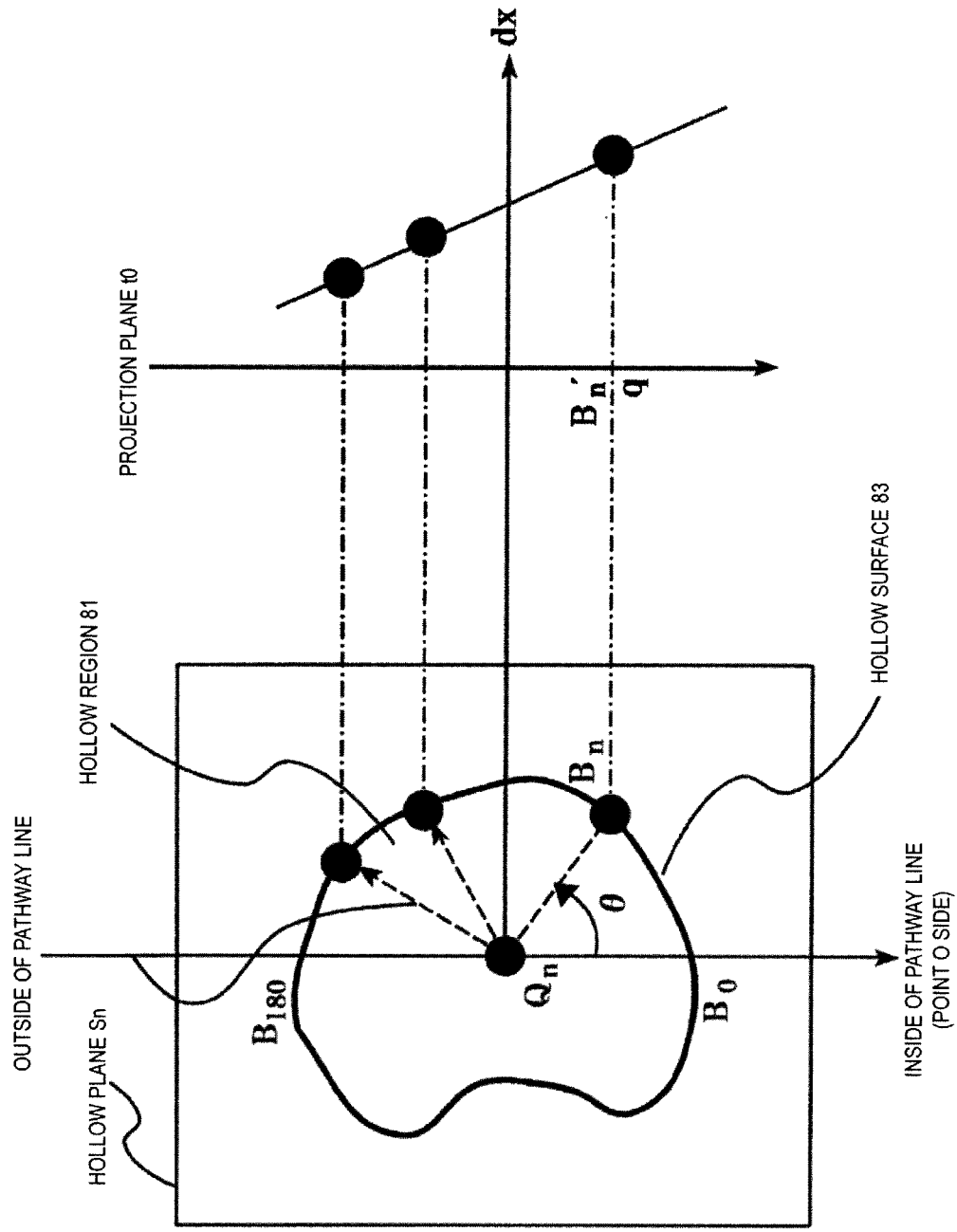
FIG. 14 is a diagram explaining the relation between a position on a hollow surface and a pixel size in the longitudinal direction.

FIG. 14 is a diagram explaining the relation between positions on the hollow surface and the longitudinal pixel sizes.

CPU 101 of the medical image processing device 100 of the second exemplary embodiment reads out the programs and data related to the pixel deformation calculation processing represented in FIG. 10 from the main memory 102 and executes the pixel deformation calculation processing based on the read-out programs and data.

It is herein assumed that the image data is downloaded from the image database 111 or the like through the network 110 and is stored in the storage device 103 of the medical image processing device 100 on the onset of executing the following processing.

In the pixel deformation calculation processing, CPU 101 of the medical image processing device 100 firstly loads panoramic image data 102l, three dimensional space coordinate data 102m that contains the coordinates of points in the three dimensional space corresponding to points on the panoramic image, and coordinate data 102n of points on the pathway line (hereinafter referred to as "pathway points") from the storage device 103, and keeps the loaded data in the main memory 102 (Step S301; 102l, 102m and 102n in FIG. 11).

The coordinate data 102a of the pathway points herein refers to the three dimensional real space coordinate data of points in each of which the pathway line intersects at right angle with a given cross-section (hereinafter referred to as "an intended hollow plane $S_n$") having a row of pixels aligned in the lateral direction on the panoramic image 71 as the hollow surface. The pathway point will be set as a pathway point on the intended hollow plane $S_n$ and is referred to as an intended pathway point $Q_n$ (see FIG. 12).

Next, CPU 101 sequentially scans the respective pixels on the panoramic image 71 and calculates the image deformation (dx/dy) for each point (pixel). The flowchart in FIG. 10 exemplifies a case that the pixels on the panoramic image 71 are firstly scanned along the lateral direction and then scanned along the longitudinal direction.

Pixel deformation occurred in the panoramic image 71 varies in accordance with how the pathway line is curved, i.e., magnitude of curve of the hollow organ. Therefore, CPU 101 firstly determines magnitude of curve.

CPU 101 calculates the pathway diameters R with respect to a curved region of the hollow organ using the coordinate data 102n of the pathway points and keeps the calculated pathway diameters R in the main memory 102 (Step S302, 102o in FIG. 11). The pathway diameter R will be herein explained with reference to FIG. 12. FIG. 12 illustrates a curved region of a hollow organ 8. A pathway line 82 is a line passing through roughly the center of the hollow organ 8. The n-th point on the pathway line 82 is expressed as $Q_n$. The pathway diameter R is a radius R of a circle passing through three points of: the intended pathway point $Q_n$; and pathway points $Q_{n-N}$ and $Q_{n+N}$ that are both separated from the intended pathway point $Q_n$ at an interval of a predetermined number of points N. The origin of the circle, passing through the pathway points $Q_n$, $Q_{n-N}$ and $Q_{n+N}$, is set as an origin O. A curved region has a gentle curve when the pathway diameter R is large, whereas a curved region has a sharp curve when the pathway diameter R is small.

CPU 101 determines how the hollow organ 82 is curved based on the calculated pathway diameter R (Step S303). For example, it is determined that the intended pathway point $Q_n$ is disposed on a gentle curve when the value of the pathway diameter R is greater than or equal to a predetermined threshold Rt. On the other hand, it is determined that the intended pathway point $Q_n$ is disposed on a sharp curve when the value of the pathway diameter R is less than the predetermined threshold Rt.

When it is determined that the intended pathway point $Q_n$ is disposed on a gentle curve (Step S303; gentle curve), CPU 101 deals with lateral-directional pixel deformation without dealing with the deformation due to curve because curve hardly contributes to pixel deformation.

In Step S304, the x-directional pixel size dx is firstly calculated for the intended pixel p and the calculated x-directional pixel size dx is kept on the main memory 102 (102p in FIG. 11). The pixel size dx is expressed by the following equation (8).

dx=distance from pathway point $Q_n$ to adjacent pathway point $Q_{n+1}$ (8)

Next in Step S305, the lateral directional pixel size dy is calculated for the intended pixel p and the calculated lateral directional pixel size dy is kept in the main memory 102 (102q in FIG. 11). The image size dy is expressed by the following equation (9).

dy=circumference of intended hollow plane $S_n$/matrix size in y-direction of panoramic image (9)

CPU 101 calculates the pixel deformation dx/dy based on the pixel sizes dx and dy calculated in Steps S304 and S305 (Step S306) and keeps the calculated pixel deformation dx/dy in the array (102r in FIG. 11).

When it is determined that the intended pathway point $Q_n$ is disposed on a sharp curve (Step S303; sharp curve), on the other hand, pixel deformation in the pathway line direction (longitudinal direction) occurs in the panoramic image 71 due to influence of the curve. Pixel deformation level due to curve depends on whether the pixel is disposed on the inside of the curve of the pathway line or on the outside of the curve of the pathway line.

Pixel deformation due to curve will be explained with reference to FIGS. 13 and 14. As illustrated in FIG. 13, on the adjacent hollow planes $S_n$ and $S_{n+1}$ of the hollow organ 8, a small distance is produced from a pixel disposed inwards of the curve on one of the hollow planes to a corresponding pixel disposed on the other (adjacent one) of the hollow planes, whereas a large distance is produced from a pixel disposed outwards of the curve on one of the hollow planes to a corresponding pixel disposed on the other (adjacent one) of the hollow planes.

In FIG. 14, the pathway line direction of the hollow plane $S_n$ is expressed along a direction perpendicular to the sheet of FIG. 14, and a situation is illustrated therein that respective points $B_n$ on the edge of the hollow region (hollow surface 83) on the hollow plane $S_n$ are projected on a projection plane $t_0$. In FIG. 14, a point $Q_n$ is an intended pathway point and a point $B_n$ is a given point on the hollow surface 83, whereas a point O corresponds to the point O in FIG. 12 (the origin of the circle fitted to the pathway line 82).

Simply put, as illustrated in FIG. 14, it is determined whether the intended pixel p on the hollow surface 83 of the hollow plane $S_n$ is disposed inwards or outwards of the curve based on magnitude of an angle θ formed by a vector $Q_nB_n$ directed from the intended pathway point $Q_n$ to a given point $B_n$ on the hollow surface and a vector $Q_nO$ directed from the point $Q_n$ to the point O. More specifically, it is determined whether the intended pixel p is disposed inwards or outwards of the curve based on a projected coordinate q of a point $B_n'$ obtained by projecting the vector $Q_nB_n$ on the vector $Q_nO$ about the point $Q_n$.

Simply put, the distance between projection coordinates of the intended hollow plane $S_n$ and the adjacent hollow plane $S_{n+1}$ at corresponding angles corresponds to a pixel size dx on the panoramic image corresponding to the point $B_n$.

First, CPU 101 calculates a distance $l_0$ between the intended pathway point $Q_n$ and the adjacent pathway point $Q_{n+i}$ and keeps the calculated distance in the main memory 102 (102s in FIG. 11). The distance $l_0$ is calculated from the coordinate data 102n of the pathway points in the three dimensional real space loaded in Step S301 (Step S307).

Next, CPU 101 calculates an average diameter r of the cross-section (hollow plane $S_n$) perpendicular to the intended pathway point $Q_n$. In other words, CPU 101 refers to the three dimensional real space coordinates of pixels with a longitudinal (x-directional) coordinate identical to that of an intended pixel on the panoramic image, and calculates distances from the intended pathway point $Q_n$ to the pixels. Subsequently, CPU 101 calculates average of the calculated distances and sets the calculated average as the average hollow radius r (Step S308). CPU 101 keeps the calculated average radius r in the main memory 102 (102t in FIG. 11). It is herein noted that the distance (average radius r) can be also calculated from the depth data.

Next, CPU 101 calculates the longitudinal pixel size dx in the intended pixel p (Step S309).

In Step S309, CPU 101 firstly calculates a projected coordinate q of the intended pixel p. The projected coordinate is calculated by the following equation (10).

q=rosθ (10)

A value of an angle θ is herein calculated based on the coordinate of the center of the pathway diameter R (coordinate of the point O), the coordinate on the pathway line (coordinate of the point $Q_n$) and the coordinate on the hollow surface (point B) (102u in FIG. 11).

CPU 101 calculates a value of the pathway-line-directional pixel size dx in the projected coordinate q using the pathway diameter R and the average hollow radius r (Step S309; 102p in FIG. 11). When the intended hollow plane $S_n$ and the adjacent hollow plane $S_{n+1}$ are disposed close to each other, it is assumed that the distance between the two planes at corresponding angles is linearly proportional to the projected coordinate q=rcos θ. Therefore, dx is calculated by the following equation (11).

$$dx = \frac{(R-q)}{R}l_0 = \frac{(R-r\cos\theta)}{R}l_0 \quad (11)$$

Next, CPU 101 calculates the y-directional pixel size dy in the intended pixel p (Step S310; 102q in FIG. 11).

Similarly to Step S305, the pixel size dy is calculated by the following equation (12).

dy=circumference of intended hollow plane $S_n$/matrix size in y-direction of panoramic image (12)

CPU 101 calculates the pixel deformation dx/dy based on the pixel sizes dx and dy calculated in Steps S309 and 310 (Step S311) and stores the calculated pixel deformation dx/dy in the array (Step S312; 102r in FIG. 11).

CPU 101 completes the pixel deformation calculation processing when the pixel deformation dx/dy is calculated for all the pixels by repeating the processing of Steps S302 to S312 for each pixel on the panoramic image as described above.

The pixel deformation dx/dy for each pixel, calculated in the pixel deformation calculation processing, is referred in executing curvature calculation in Step S202 of the lesion candidate region detection processing in FIG. 3.

For example, CPU 101 calculates the deformation adjusted parameters P2_x and P2_y for the parameter P2 based on the following equations (13).

$$\left.\begin{array}{l}P2\_x = A \times P1 \times dx/dy \\ P2\_y = A \times P1\end{array}\right\} \quad (13)$$

In the above equation, P2_x is inter-distance between differentiation reference points in the longitudinal direction, whereas P2_y is inter-distance between differentiation reference points in a direction perpendicular to the longitudinal direction. A curvature value is obtained by calculating the following equations (14) using the deformation adjusted parameters P2_x and P2_y and calculating the shape index using the aforementioned equations (4), (5) and (6).

$$f_{xx} = \frac{f(x+P2\_x, y) + f(x-P2\_x, y) - 2f(x, y)}{(P2\_x)^2}$$
$$f_{yy} = \frac{f(x, y+P2\_y) + f(x, y-P2\_y) - 2f(x, y)}{(P2\_y)^2}$$
$$f_{xy} = \frac{f(x+P2\_x, y+P2\_y) - f(x-P2\_x, y+P2\_y) - f(x+P2\_x, y-P2\_y) + f(x-P2\_x, y-P2\_y)}{P2\_x \cdot P2\_y} \quad (14)$$

Thus, curvature calculation can be executed based on a length in the real space even for a deformed image such as an panoramic image by correcting the parameter P2 using the pixel deformation dx/dy in executing the curvature calculation.

It is herein noted that the deformation adjusted parameters P2_x and P2_y can be also calculated by the following equations (15).

$$P2\_x = A \times P1 \times dx$$
$$P2\_y = A \times P1 \times dy \quad (15)$$

Figure 15:
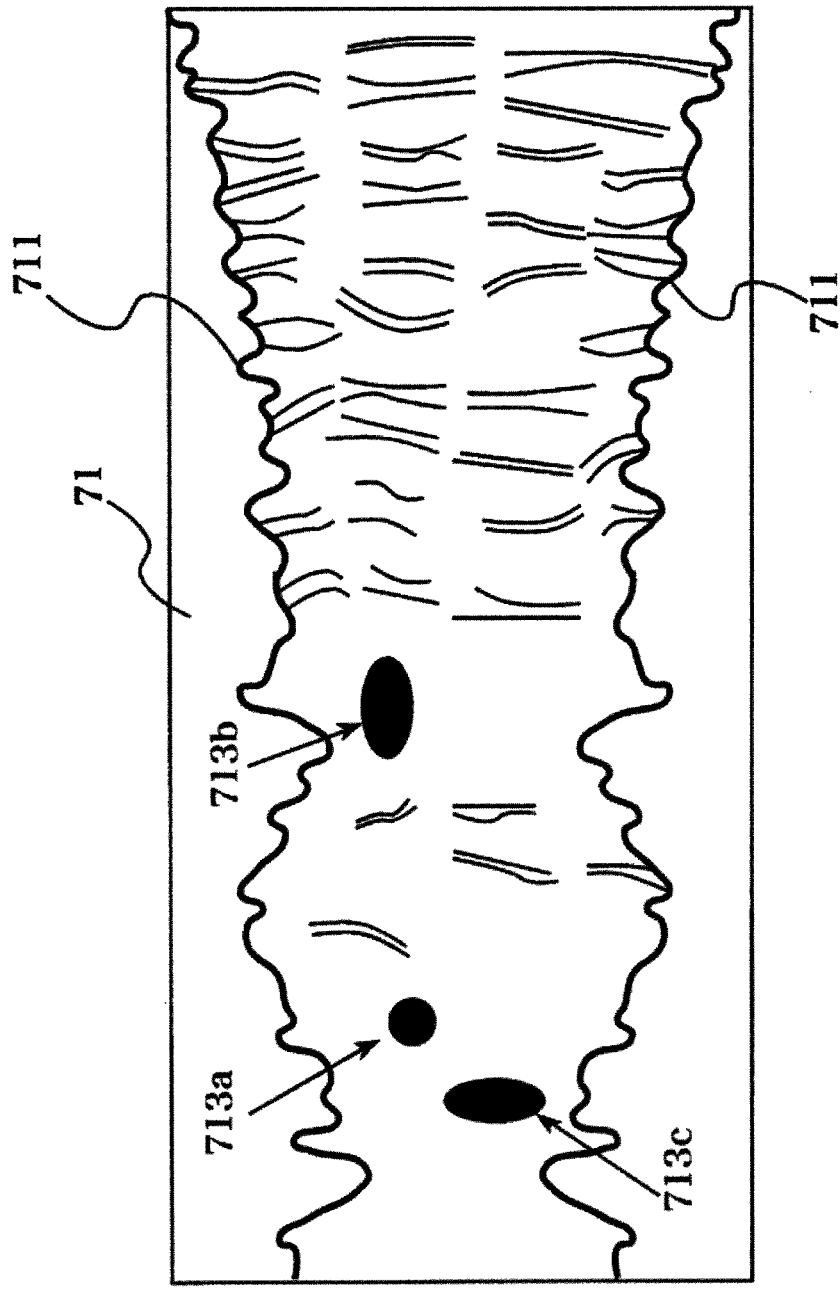
FIG. 15 is a diagram illustrating a display example of lesion candidate regions to be obtained in executing a lesion candidate detection processing based on a deformation adjusted parameter obtained by correcting pixel deformation.

FIG. 15 is a diagram illustrating a display example of lesion candidate regions to be obtained when the lesion candidate detection processing is executed using the deformation adjusted parameters P2_x and P2_y.

As illustrated in FIG. 15, lesion candidate regions 713a, 713b and 713c are distinguishably displayed on the panoramic image 71.

In FIG. 15, the marking 713a indicates a lesion candidate region in a less deformed region; the marking 713b indicates a transversely deformed lesion candidate region; and the marking 713c indicates a vertically deformed lesion candidate region. Simply put, even if being a circular polyp in the real space, a region transversely deformed by the influence of the curve of a hollow organ in the real space cannot be detected as a lesion candidate without executing a lesion candidate detection using the deformation adjusted parameters. However, the shape in the real space can be properly assessed by executing curvature calculation using the deformation adjusted parameters P2_x and P2_y as executed in the present exemplary embodiment. Similarly, the shape in the real space can be properly assessed for a vertically deformed region such as the marking 713c.

As described above, in the image processing system 1 of the second exemplary embodiment, CPU 101 calculates the deformation amount (dx/dy) of each pixel in both of the longitudinal and lateral directions by executing the pixel deformation calculation processing, corrects the parameter using the calculated deformation amount, and calculates the deformation adjusted parameters (P2_x, P2_y) in executing the lesion candidate detection processing for an panoramic image. Subsequently, CPU 101 executes curvature calculation and the like using the deformation adjusted parameters and detects lesion candidate regions.

Therefore, it is possible to properly assess the shape of the organ surface in the real space for even a longitudinally and/or laterally deformed image such as an panoramic image. Accordingly, detection accuracy will be enhanced for lesion candidate regions.

It is noted that the second exemplary embodiment exemplifies a case of correcting the parameter P2 indicating the inter-distance between differentiation reference points. However, deformation correction may be similarly executed for the parameter P3 and the parameter P4.

(Third Exemplary Embodiment)

Next, the image processing system 1 of a third exemplary embodiment will be explained. The hardware configuration of the image processing system 1 of the third exemplary embodiment is the same as that of the image processing system 1 of the first exemplary embodiment illustrated in FIG. 1. Therefore, explanation thereof will be hereinafter omitted, and a given component shared between the first and third exemplary embodiments will be explained while being given the same reference numeral.

In the third exemplary embodiment, a predetermined processing is executed in consideration of deformation of an panoramic image in setting parameters, similarly to the second exemplary embodiment. In the second exemplary embodiment, deformation of an image due to curve is regulated. By contrast, a processing related to deformation of an panoramic image in a more sharply curved region will be explained in the third exemplary embodiment.

In generating an panoramic image, a cross-sectional orientation is corrected for a sharply curved hollow organ 8 in order to prevent intersection among hollow cross-sections.

Figure 16:
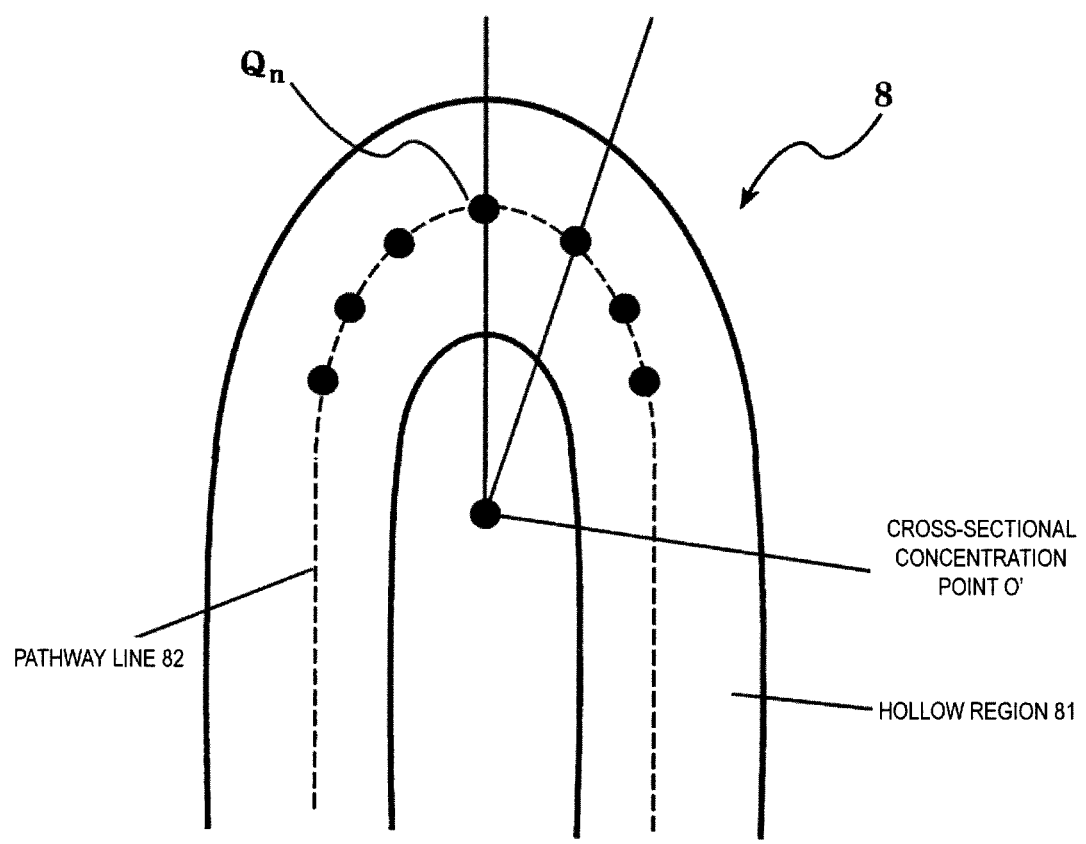
FIG. 16 is a diagram explaining cross-sectional correction in a sharply curved region.

FIG. 16 is a diagram explaining cross-sectional correction in a sharply curved region.

As illustrated in FIG. 16, the following technique is used for a sharply curved region of the hollow organ 8. Simply put, a given cross-sectional concentration point O' is set in a position that exists outsides a hollow region 81 and simultaneously inwards of the curve of a pathway line 82, and such an intended hollow plane $S_n$ is selected that passes through a line segment $O'Q_n$ connecting the cross-sectional concentration point O' and the intended pathway point $Q_n$.

When the above cross-sectional correction is executed, the intended hollow plane $S_n$ may be greatly inclined without intersecting at right angle with the tangent line of the pathway line on the intended pathway point $Q_n$. Therefore, it may be difficult to execute linear approximation for the distance between projection coordinates of the intended hollow plane $S_n$, and the adjacent hollow plane $S_{n+1}$ at corresponding angles unlike the technique of the second exemplary embodiment.

In view of the above, according to the present third exemplary embodiment, the longitudinal pixel size dx in the intended pixel p is obtained as the distance between two points in the three dimensional real space that respectively correspond to the intended pixel p and a pixel longitudinally adjacent to the intended pixel p on an panoramic image (hereinafter referred to as "adjacent pixel $p_{next}$").

Figure 17:
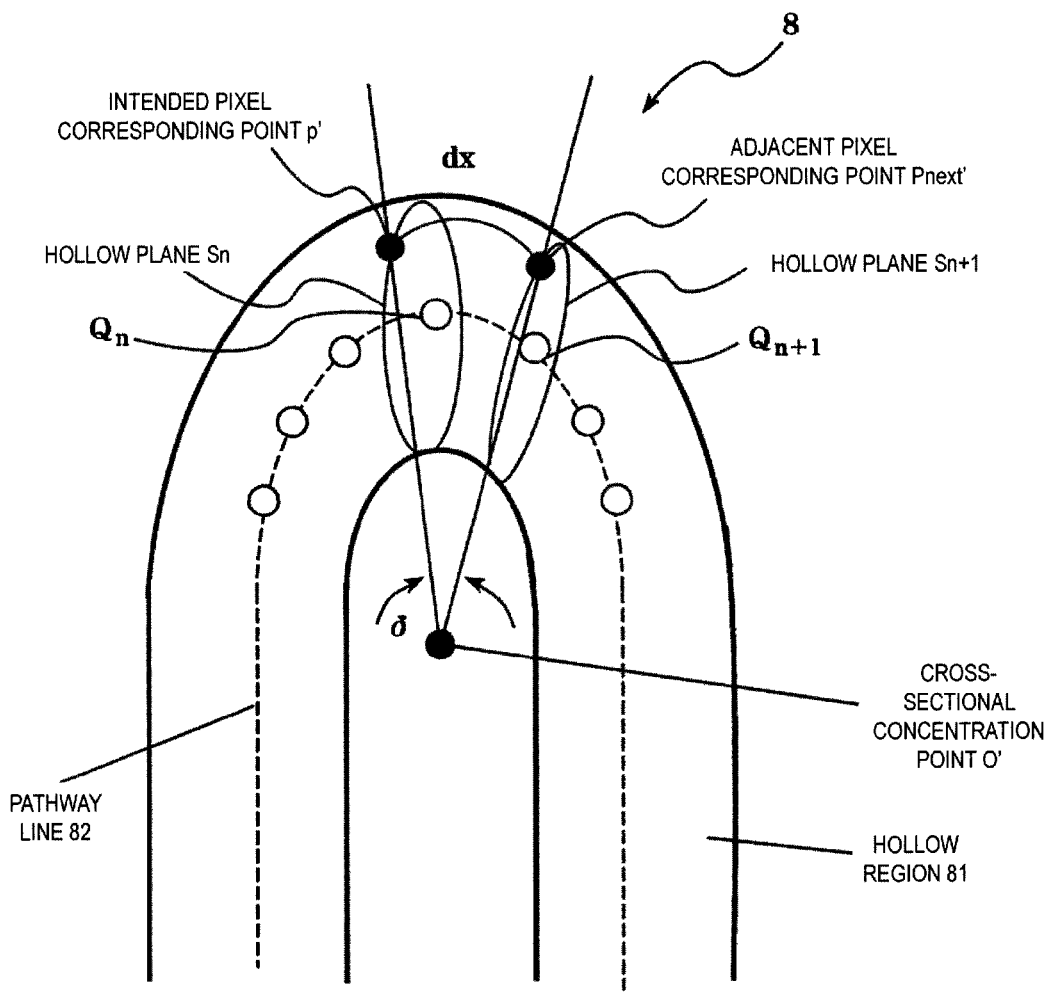
FIG. 17 is a diagram explaining the positional relation among points in calculating pixel deformation in a third exemplary embodiment.

FIG. 17 is a diagram explaining the positional relation among points in the hollow organ 8 that is the source of an panoramic image as a lesion candidate object in the third exemplary embodiment.

In a sharply curved region of the hollow organ 8 as illustrated in FIG. 17, points in the three dimensional real space, which respectively correspond to the intended pixel p on the hollow plane $S_n$ and the pixel $p_{next}$ (corresponding to the intended pixel p) on the adjacent hollow plane $S_{n+1}$, are respectively referred to as intended pixel corresponding points p' and $p_{next}$'.

Then, the length of a circular arc connecting the two intended pixel corresponding points p' and $p_{next}$' is calculated and the calculated circular arc length is set as a distance dx for approximating the distance dx between the intended pixel corresponding points p' and $p_{next}$' in the three dimensional real space to be the length of a curve arranged along the pathway line 82.

Figure 18:
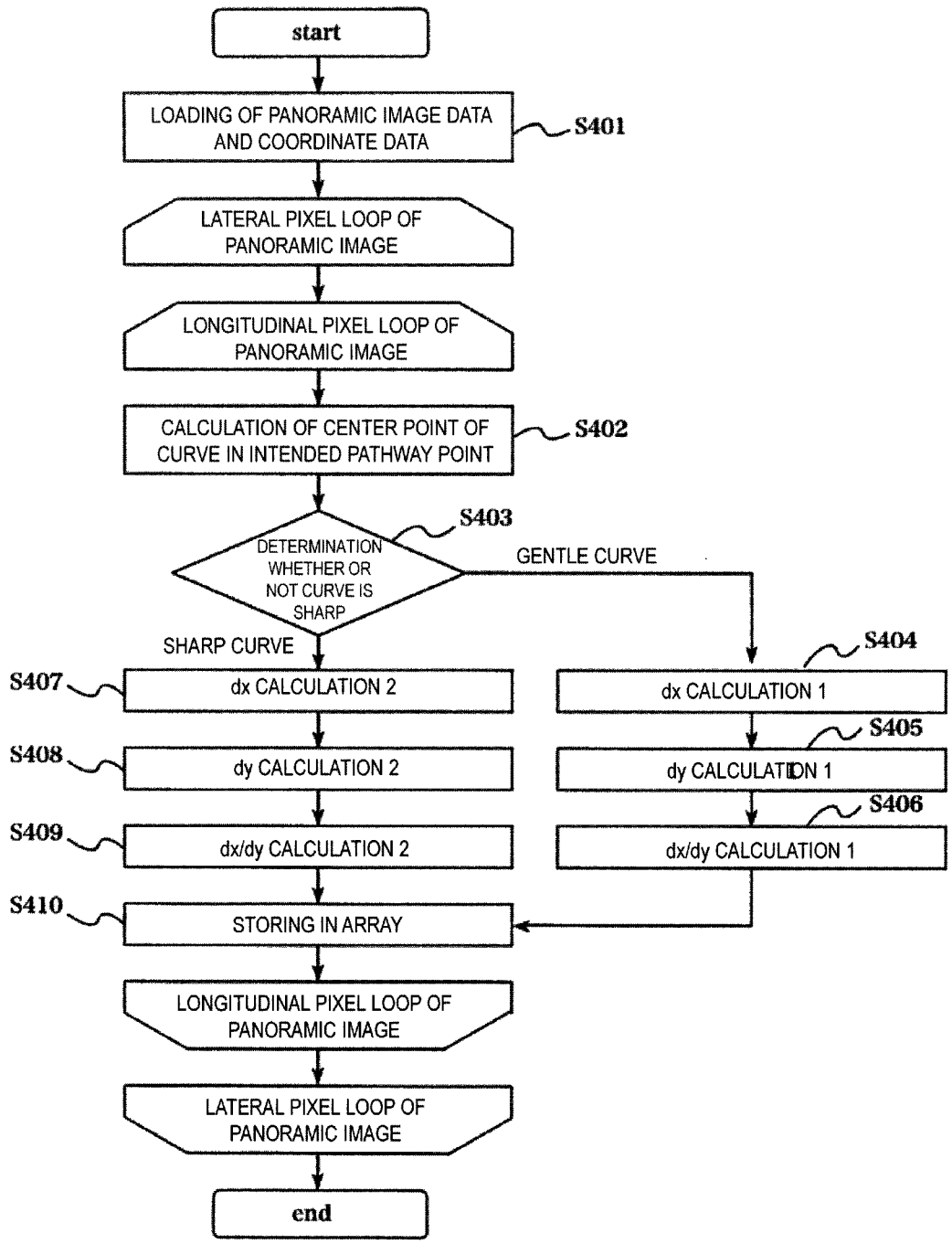
FIG. 18 is a flowchart explaining the flow of a pixel deformation calculation processing in the third exemplary embodiment.

In response to this, according to the third exemplary embodiment, the pixel deformation (dx/dy) is calculated for each pixel using the pixel deformation calculation processing represented in FIG. 18 and the deformation adjusted parameters (P2_x, P2_y) obtained by correcting the parameter P2 are calculated based on the calculated pixel deformation (dx/dy) when the parameter setting processing of Step S201 is executed in the lesion candidate detection processing of the first exemplary embodiment (see FIG. 3).

FIG. 18 is a flowchart explaining the flow of the pixel deformation calculation processing in the third exemplary embodiment.

Figure 19:
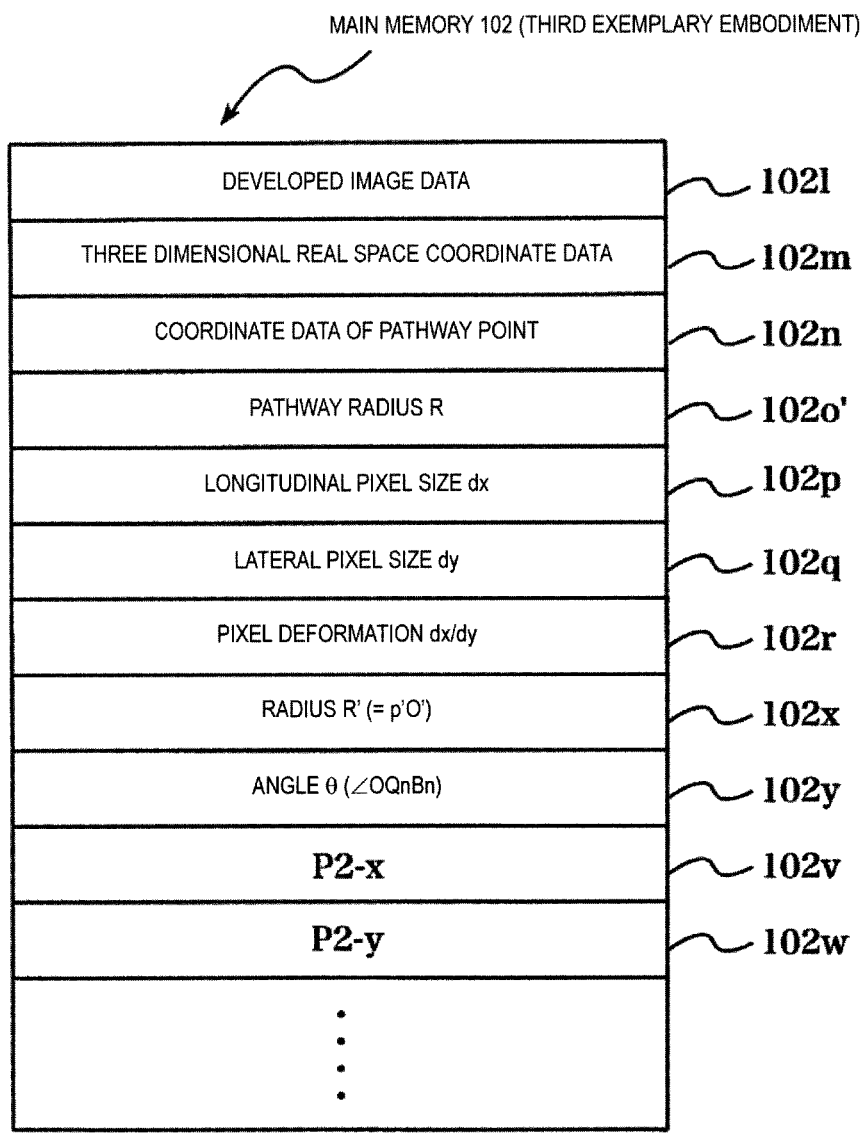
FIG. 19 is a data configuration diagram of the main memory 102 (third exemplary embodiment).

FIG. 19 is a diagram representing the data to be kept in RAM of the main memory 102 in executing the pixel deformation calculation processing.

CPU 101 of the medical image processing device 100 of the third exemplary embodiment reads out the programs and data related to the pixel deformation calculation processing represented in FIG. 18 from the main memory 102, and executes the pixel deformation calculation processing based on the read-out programs and data.

It is herein assumed that the image data is downloaded from the image database 111 or the like through the network 110 and is stored in the storage device 103 of the medical image processing device 100 on the onset of executing the following processing.

In the pixel deformation calculation processing represented in FIG. 18, CPU 101 of the medical image processing device 100 firstly loads the panoramic image data, the three dimensional real space coordinate data containing the third dimensional real space coordinates of the corresponding points on the panoramic image, and the coordinate data of the pathway points from the storage device 103 and keeps the loaded data in the main memory 102, similarly to Step S301 of the pixel deformation calculation processing represented in FIG. 10 (Step S401 and 102*l*, 102*m* and 102*n* in FIG. 19).

Next, CPU 101 sequentially scans the respective pixels on the panoramic image 71 and calculates the pixel deformation (dx/dy) of each point (pixel). The flowchart of FIG. 18 exemplifies a case that the panoramic image is firstly scanned along the lateral direction and then scanned along the longitudinal direction.

Similarly to the second exemplary embodiment, CPU 101 firstly determines magnitude of the curve because pixel deformation occurred in the panoramic image 71 depends on how the pathway line 82 is curved, i.e., magnitude of the curve of the hollow organ 8.

CPU 101 firstly calculates the distance between the cross-sectional concentration point O' and the intended pathway point $Q_n$' as the pathway diameter R and keeps the calculated distance in the main memory 102 (102*o*' in FIG. 19). Next, CPU 101 determines magnitude of the curve based on the magnitude of the pathway diameter R (Step S402).

When the pathway diameter R is large, this indicates a gentle curved region. When the pathway diameter R is small, this indicates a sharply curved region.

Similarly to Step S303 in FIG. 10, CPU 101 determines how the pathway line is curved based on the calculated pathway diameter R (Step S403). For example, when the magnitude of the pathway diameter R is greater than or equal to a predetermined threshold Rt, it is determined that the intended pathway point $Q_n$ is disposed on a gentle curve. When the magnitude of the pathway diameter R is less than the predetermined threshold Rt, it is determined that the intended pathway point $Q_n$ is disposed on a sharp curve.

When it is determined that the intended pathway point $Q_n$ is disposed on a gentle curve (Step S403; gentle curve), CPU 101 calculates the x-directional pixel size dx in the intended pixel p and the y-directional pixel size dy in the intended pixel p using the aforementioned equations (8) and (9) and keeps the calculated sizes in the main memory 102, similarly to Steps S304, S305 and S306 in FIG. 9 (Steps S404 and S405, 102*p* and 102*q* in FIG. 19). Then, CPU 101 calculates the pixel deformation dx/dy and stores the calculated pixel deformation in the array (Step S406 to Step S410; 102*r* in FIG. 19).

On the other hand, the processing proceeds to Step S407 when it is determined that the intended pathway point $Q_n$ is disposed on a sharp curve (Step S403; sharp curve). In Step S407, CPU 101 calculates the length (pixel size dx) of a circular arc between two intended pixel corresponding points p' and $p_{next}$' illustrated in FIG. 17.

In other words, CPU 101 firstly calculates distance p' O' based on the three dimensional real space coordinate data of the intended pixel corresponding point p' and the cross-sectional concentration point O', and sets the calculated distance as radius R'. CPU 101 keeps the calculated radius R' in the main memory 102 (102*x* in FIG. 19).

Next, CPU 101 calculates an angle δ formed by three points, i.e., the intended pixel corresponding point p', the cross-sectional concentration point O' and the adjacent pixel corresponding point $p_{next}$' and keeps the calculated angle in the main memory 102 (102*y* in FIG. 19).

The angle δ is calculated by the following equation (16) where a vector directed from the point O' to the point P' is set as a vector O' p' and a vector directed from the point O' to the point $p_{next}$' is set as a vector O' $p_{next}$'.

$$\delta = \arccos\left(\frac{O'p' \cdot O'p'_{next}}{|O'p'| \cdot |O'p'_{next}|}\right) \quad (16)$$

Subsequently, CPU 101 calculates the length of the circular arc using the following equation (17) and keeps the calculated length in the main memory 102 (Step S407; 102*p* in FIG. 19).

$$dx = R'\delta \quad (17)$$

Next, CPU 101 calculates the lateral pixel size dy in the intended pixel p using the following equation (18) and keeps the calculated lateral pixel size dy in the main memory 102 (Step S408; 102*q* in FIG. 19).

dy=circumference of intended hollow plane $S_n$/matrix size in y-direction of panoramic image $\quad$ (18)

CPU 101 calculates the pixel deformation dx/dy based on the pixel sizes dx and dy calculated in Steps S407 and S408 (Step S409) and stores the calculated pixel deformation in the array (Step S410; 102*r* in FIG. 19).

CPU 101 completes the pixel deformation calculation processing when the pixel deformation dx/dy is calculated for all the pixels by repeating the processing of Steps S402 to S410 for each pixel on the panoramic image as described above.

The pixel deformation dx/dy for each pixel, calculated in the pixel deformation calculation processing, is referred in executing curvature calculation of Step S202 in the lesion candidate region detection processing in FIG. 3. Calculation of the deformation adjusted parameters (P2_x, P2_y) is similar to that in the second exemplary embodiment. Therefore, explanation thereof will be hereinafter omitted.

Similarly to the display example illustrated in FIG. 15, lesion candidate regions can be properly and distinguishably displayed regardless of deformation of an panoramic image (see the lesion candidate regions 713a, 713b and 713c in FIG. 15) by executing the lesion candidate detection processing using the deformation adjusted parameters P2_x and P2_y in an panoramic image (an panoramic image processed with cross-sectional correction) to be generated by setting the hollow plane $S_n$ about the cross-sectional concentration point O' in a sharply curved region of a hollow organ as described above.

As described above, according to the image processing system 1 of the third exemplary embodiment, the longitudinal pixel size dx of a hollow organ is calculated as the length of a circular arc between adjacent pixel corresponding points in an panoramic image that cross-sectional correction is executed for a curved region. Therefore, it is possible to properly assess the shape of an panoramic image in the real space even if cross-sectional correction is executed for the panoramic image because of a sharp curve included in the curved region. Detection accuracy will be herein enhanced for lesion candidate regions.

It is noted that the technique in the third exemplary embodiment for calculating the pixel size dx using a circular arc may be applied to an panoramic image of a relatively gently curved region that has not been processed with cross-sectional correction, such as the panoramic image of the second exemplary embodiment.

Further, the third exemplary embodiment also exemplifies a case that correction is executed for the parameter P2 indicating the inter-distance between differentiation reference points. However, deformation correction may be similarly executed for the parameter P3 and the parameter P4.

(Fourth Exemplary Embodiment)

The first to third exemplary embodiments exemplify the cases of lesion candidate detection regarding an panoramic image of a hollow organ. However, the image processing device of the invention may be applied for executing other image display methods. In a fourth exemplary embodiment, a case is explained that the invention is applied to a virtual endoscope image.

FIG. 20 is a diagram explaining a virtual endoscope image. FIG. 20 (a) illustrates a hollow organ under the condition that the longitudinal direction thereof is illustrated along the vertical direction. FIG. 20 (b) is an example of the virtual endoscope image of the hollow organ in FIG. 20 (a).

The virtual endoscope image is an image 75 (FIG. 20 (b)) obtained by projecting a view with a predetermined directional range ($\theta_{view}$) as an angle-of-sight from a given point-of-sight $p_0$ set in the inside of a hollow region v illustrated in FIG. 20 (a) on a planar projection plane $s_0$.

A pixel value of each point (hereinafter referred to as "intended pixel p") of the virtual endoscope image 75 is a shadow value given based on the distance between the point-of-sight $p_0$ and an intended pixel corresponding point p'. For example, the intended pixel corresponding point p' is a voxel that a virtual light beam called "ray" reaches when the ray is irradiated from the point-of-sight $p_0$ to the intended pixel p in the three dimensional real space coordinate. The voxel, which is the intended pixel corresponding point p', has a pixel value within a predetermined threshold range.

A method of calculating curvature based on concentration gradient in each point of the virtual endoscope image 75 can be suggested as an example of the methods of calculating curvature with respect to the virtual endoscope image 75.

However, the following two kinds of deformation are produced in the virtual endoscope image 75 to be generated by a generally used perspective projection.

The two kinds of deformation are: deformation in accordance with the distance from the point-of-sight $p_0$ of a projection object; and deformation in accordance with the angle of a direction from the point-of-sight $p_0$ to the projection object with respect to the projection surface.

Therefore, it is necessary to correct the inter-distance between differentiation reference points (parameter P2) to be used for curvature calculation based on the pixel value calculated with the aforementioned method in executing the lesion candidate region detection processing with respect to the virtual endoscope image 75.

Figure 21:
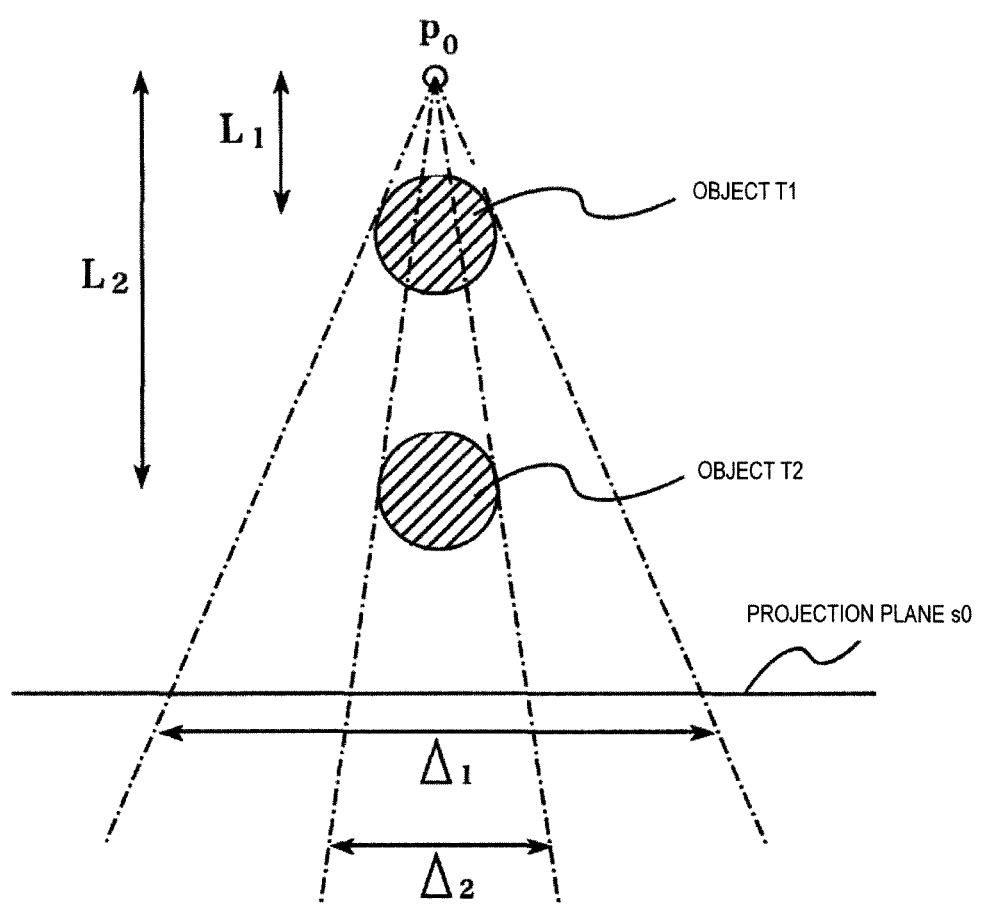
FIG. 21 is a diagram explaining deformation due to distance from a point-of-view to a projected object.
Figure 22:
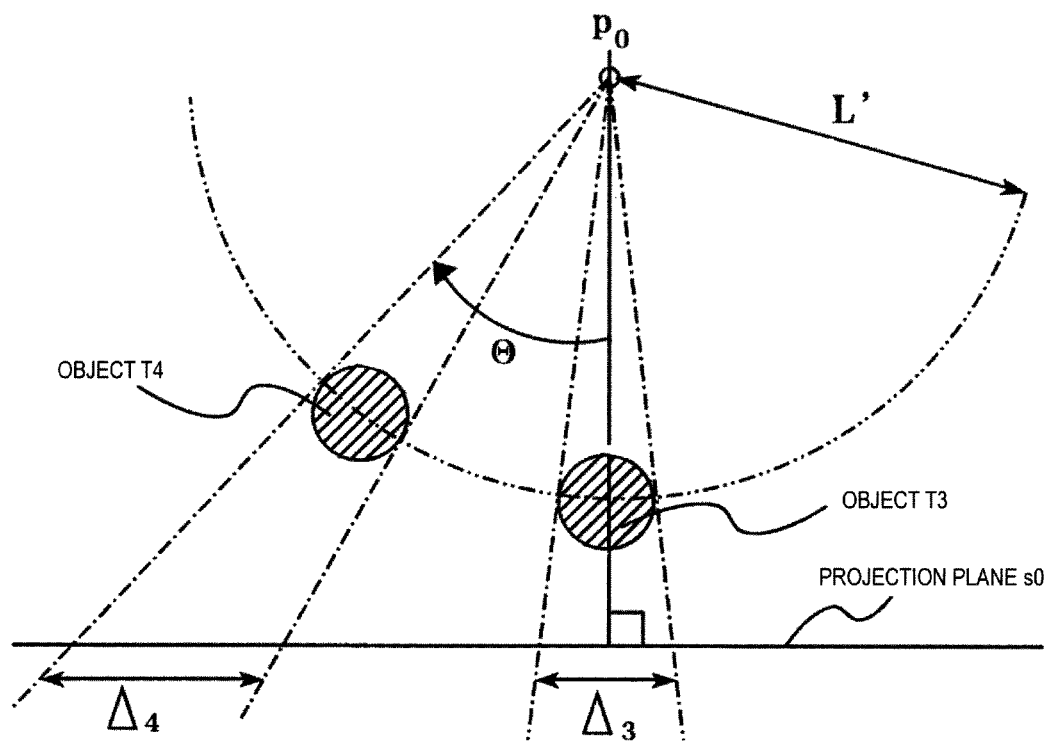
FIG. 22 is a diagram explaining deformation to be produced in end portions of the virtual endoscope image.

FIG. 21 is a diagram explaining deformation due to the distance from the point-of-sight to the projection object. FIG. 22 is a diagram explaining deformation occurred in the edges of the virtual endoscope image.

As illustrated in FIG. 21, when the projection object is projected on a projection plane $s_0$, the size of the projected image varies in accordance with the distance from the point-of-sight $p_0$. Two objects T1 and T2, having the same size, are disposed in the same direction but at different distances from the point-of-sight $p_0$ towards the projection plane $s_0$. In this case, the distance from the point-of-sight $p_0$ to the object T1 is set as distance $L_1$, whereas the distance from the point-of-sight $p_0$ to the object T2 is set as distance $L_2$. Further, the sizes of the images to be projected on the projection plane $s_0$ are respectively set as sizes $\Delta_1$ and $\Delta_2$. When the sizes $\Delta_1$ and $\Delta_2$ are compared, the object T1 positioned closer to the point-of-sight $p_0$ is projected on the projection plane $s_0$ as a larger image ($\Delta_1 > \Delta_2$). This results in image deformation. Therefore, it is necessary to set the inter-distance between differentiation reference points (parameter P2) in a given intended pixel p so that the same inter-distance between differentiation reference points can be obtained in a given intended pixel corresponding point p' when curvature calculation is executed.

Further, as illustrated in FIG. 22, when normal lines are extended towards the objects T3 and T4 as the projection targets from the point-of-sight $p_0$ to the projection plane $s_0$, an angle formed by each normal line is set as $\Theta$. Further, the sizes of images to be projected on the projection plane $s_0$ are respectively set as $\Delta_3$ and $\Delta_4$. When the sizes $\Delta_3$ and $\Delta_4$ are compared, an image projected on the projection plane $s_0$ gets larger in proportion to increase in the angle $\Theta$ ($\Delta_4 > \Delta_3$). This results in image deformation. Therefore, it is necessary to correct the value of the inter-distance between differentiation reference points (parameter P2) in the edges of the virtual endoscope image 75 to be greater than that in the center part of the image.

Correction of the parameter 2 (inter-distance between differentiation reference points) in the virtual endoscope image 75 generated with perspective projection will be hereinafter explained with reference to FIGS. 23, 24 and 25.

Figure 23:
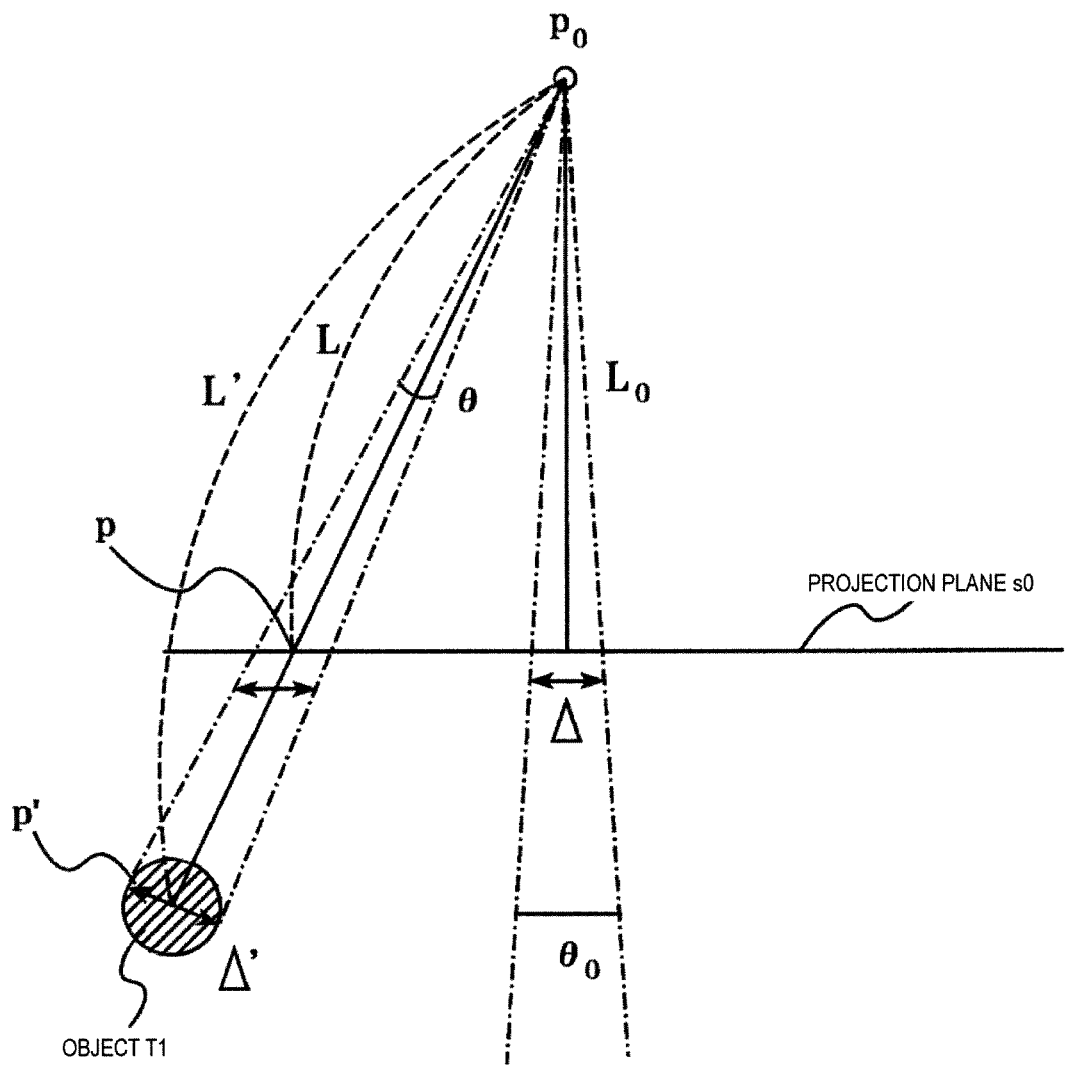
FIG. 23 is a diagram explaining perspective projection.

FIG. 23 is a diagram explaining perspective projection.

Figure 24:
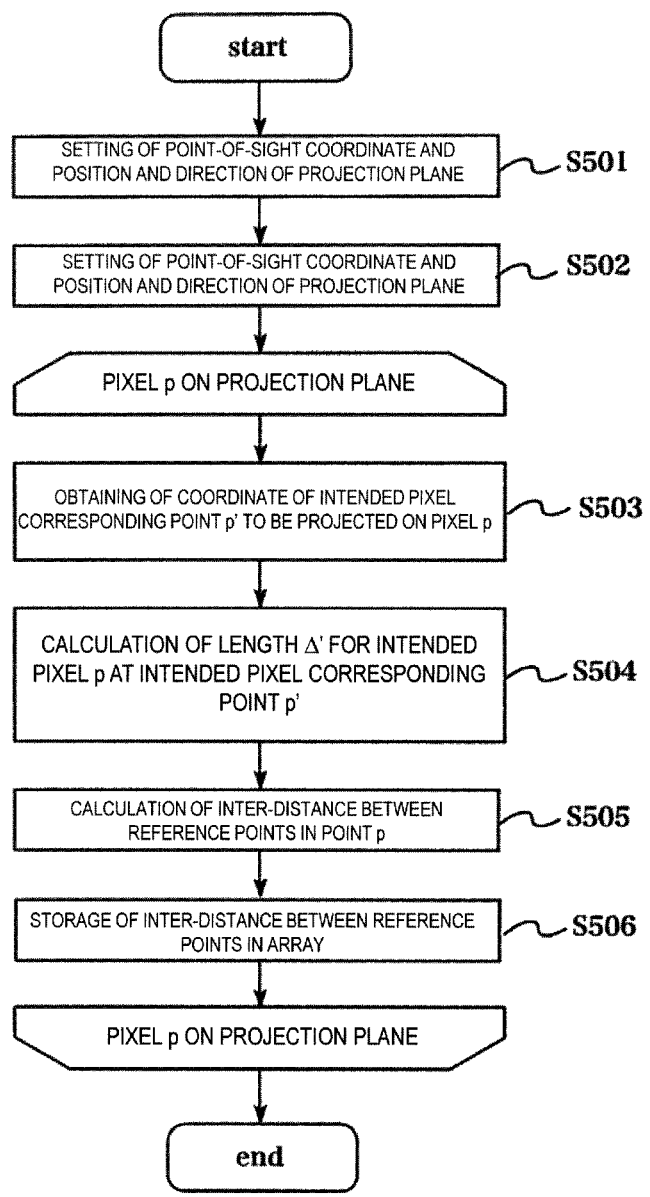
FIG. 24 is a flowchart representing the flow of a processing of calculating inter-distance between differentiation reference points in the virtual endoscope image.

FIG. 24 is a flowchart representing the flow of the processing of calculating the inter-distance between differentiation reference points with respect to the virtual endoscope image 75.

Figure 25:
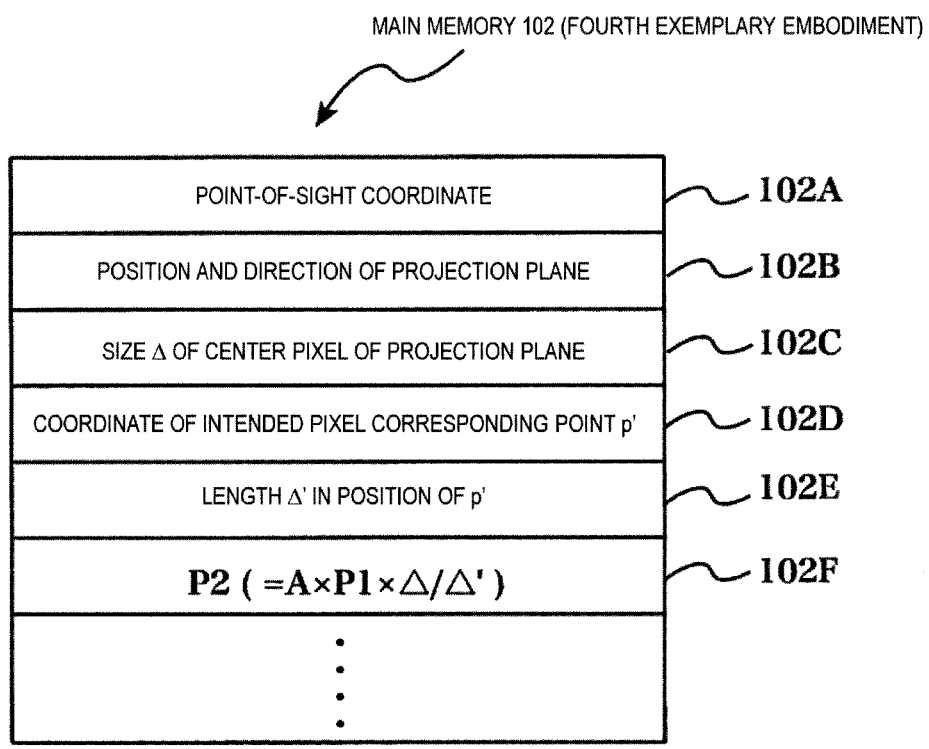
FIG. 25 is a data configuration diagram of the main memory 102 (fourth exemplary embodiment).

FIG. 25 is a diagram representing the data to be kept in RAM of the main memory 102 in executing the processing of calculating the inter-distance between differentiation reference points.

In FIG. 23, the following settings are established: $p_0$ is a point-of-sight; $s_0$ is a projection plane; $\Delta$ is the length of an edge (pixel size) of a pixel positioned in the center of the projection plane $s_0$ (hereinafter referred to as "center pixel"); $L_0$ is the distance between the point-of-sight $p_0$ and the center pixel; and $\theta_0$ is the angle about the point-of-sight $p_0$ that is formed by the both ends of the center pixel and the point-of-sight $p_0$.

Further, the following settings are established; p is an intended pixel; $\Delta'$ is the length of the projection object T1 in an intended pixel corresponding point p'; L' is the distance between the point-of-sight $P_0$ and the intended pixel corresponding point p'; and $\theta$ is the angle about the point-of-sight $p_0$ that is formed by the both ends of the intended pixel p and the point-of-sight $p_0$.

In the processing of calculating the inter-distance between differentiation reference points represented in FIG. 24, CPU 101 sets the coordinate of the point-of-sight $p_0$ and the position and direction of the projection plane $s_0$ and keeps the set coordinate, position and direction in the main memory 102 (Step S501; 102A and 102B in FIG. 25). The projection plane $s_0$ can be set based on the distance $L_0$ from the point-of-sight $p_0$ and a vector connecting the point-of-sight $p_0$ and the center pixel.

Next, CPU 101 calculates the length of an edge of the center pixel on the projection plane $s_0$ (pixel size $\Delta$) and keeps the calculated length in the main memory 102 (Step S502; 102C in FIG. 25). The pixel size $\Delta$ can be obtained by the following equation (19).

$$\Delta = L_0 \theta_0 \qquad (19)$$

CPU 101 repeats the processing of the following Steps S503 to S506 for each point (intended pixel p) on the projection plane $s_0$.

First, CPU 101 obtains the coordinate of the intended pixel corresponding point p' to be projected on the intended pixel p (Step S503). In other words, CPU 101 irradiates the intended pixel p with the ray from the point-of-sight $p_0$ and obtains the coordinate of an irradiated voxel having a brightness value within a threshold range as the coordinate of the intended pixel corresponding point p'.

Next, CPU 101 calculates the length $\Delta'$ for the intended pixel p at the position of the intended pixel corresponding point p' and keeps the calculated length in the main memory 102E (Step S504; 102E in FIG. 25).

As illustrated in FIG. 23, the length $\Delta'$ can be calculated based on the distance L' between the intended pixel corresponding point p' and the point-of-sight $P_0$ and the angle $\theta$ formed by the both end points of the pixel p' and the point-of-sight $p_0$ when the intended pixel p is viewed from the point-of-sight $p_0$. Simply put, the length $\Delta'$ is expressed by the following equation (20).

$$\Delta' = L'\theta \qquad (20)$$

The angle $\theta$ can be herein calculated based on the coordinate of the intended pixel p, the distance L between the intended pixel p and the point-of-sight $p_0$, the distance $L_0$ between the center pixel and the point-of-sight $p_0$, and the length $\Delta$ of an edge of the center pixel.

CPU 101 calculates the inter-distance P2 between differentiation reference points in the intended pixel p (Step S505). When the inter-distance P2 between differentiation reference points in the center pixel follows the relation of "P2=A×P1" (the aforementioned equation (1)), the inter-distance P2 between differentiation reference points in the intended pixel p can be expressed by the following equation (21).

$$P2 = A \times P1 \times \frac{\Delta}{\Delta'} = A \times P1 \times \frac{L_0 \theta_0}{L'\theta} \qquad (21)$$

CPU 101 stores the inter-distance P2 between differentiation reference points for the intended pixel p calculated in Step S505 in the array (Step S506; 102F in FIG. 25).

CPU 101 completes the processing of calculating the inter-distance between differentiation reference points represented in FIG. 24 when the inter-distance P2 between differentiation reference points are calculated for all the pixels p by repeating the processing of Steps S503 to S506 for each pixel in the virtual endoscope image as described above.

Subsequently, CPU 101 calculates a curvature value (shape index) using the inter-distance P2 between differentiation reference points of each pixel calculated with the aforementioned processing steps in the lesion candidate region detection processing represented in FIG. 3 and detects lesion candidates.

As described above, according to the image processing system 1 of the fourth exemplary embodiment, the inter-distance P2 between differentiation reference points is corrected in the virtual endoscope image to be generated with perspective projection in consideration of image deformation. Then, legion candidates are detected using the corrected inter-distance P2 between differentiation reference points.

Consequently, the shape of the organ surface can be properly assessed even when the lesion candidate detection processing is executed for a virtual endoscope image, and detection accuracy will be thereby enhanced for lesion candidate regions.

It is noted that correction of the inter-distance between differentiation reference points in a virtual endoscope image with perspective projection has been described in the fourth exemplary embodiment. However, some of the virtual endoscope images are processed with correction of deformation occurred in the edges of the images (i.e., deformation in accordance with the angle of a direction from the point-of-sight to the projection object with respect to the projection surface) (e.g., JP-A-7-296184). In this case, image deformation depends only on the distance from a point-of-sight. Therefore, it is required to execute correction that depends only on the distance from the point-of-sight for the inter-distance between differentiation reference points (parameter P2). The inter-distance between differentiation reference points is expressed by the following equation (22).

$$P2 = A \times P1 \times \frac{L_0}{L'} \qquad (22)$$

The preferred exemplary embodiments of the image processing device according to the invention have been explained above. However, the invention is not limited to the aforementioned exemplary embodiments. For example, the techniques explained in the first to fourth exemplary embodiments may be arbitrarily combined. Further, it is apparent for those skilled in the art that a variety of changes and modifications can be made for the invention without departing from the technical scope disclosed in the present application. It should be understood that those changes and modifications are also incorporated in the technical scope of the invention.

DESCRIPTION OF REFERENCE NUMERALS AND SIGNS

| | |
|---|---|
| 1 | Image processing system |
| 100 | Medical image processing device |
| 101 | CPU |
| 102 | Main memory |

-continued

| | |
|---|---|
| 103 | Storage device |
| 104 | Communication I/F |
| 105 | Display memory |
| 106 | I/F |
| 107 | Display device |
| 108 | Mouse (external device) |
| 109 | Input device |
| 110 | Network |
| 111 | Image database |
| 71 | Panoramic image |
| 713 | Lesion candidate region |
| 72 | Parameter setting window |
| 721 | Mode list |
| 722 | Numerical value input box |
| 8 | Hollow organ |
| 81 | Hollow region |
| 82 | Pathway line |
| 83 | Hollow surface |
| $Q_n$ | Pathway point |
| $S_n$ | Hollow plane |
| P | Intended pixel |
| dx | Longitudinal pixel size |
| dy | Lateral pixel size |
| O | Origin of circle fitted to pathway point |
| O' | Cross-sectional concentration point |

The invention claimed is:

1. An image processing device for detecting a lesion candidate region from a medical image, comprising:
parameter setting means for setting a parameter to be used for detecting the lesion candidate region; and
lesion candidate region detecting means for assessing the medical image using the parameter set by the parameter setting means and detecting the lesion candidate region based on a result of the assessment,
wherein the parameter setting means includes
parameter inputting means configured to input a first parameter indicating dimension of the lesion, and
second parameter calculating means configured to calculate a second parameter based on the first parameter indicating the dimension of the lesion, and
wherein the lesion candidate region detecting means includes
lesion candidate region extracting means configured to (i) calculate a feature amount indicating a shape of an organ surface, by using the second parameter in the medical image and (ii) extract the lesion candidate region based on the feature amount calculated based on the second parameter which in turn was calculated based on the first parameter indicating the dimension of the lesion.

2. The image processing device recited in claim 1, wherein the lesion candidate detecting means further includes:
false-positive deleting means configured to delete a false-positive region by assessing a predetermined feature amount of the lesion candidate region extracted by the lesion candidate region extracting means and deleting the lesion candidate region when the lesion candidate region is determined as the false-positive region.

3. The image processing device recited in claim 2, wherein the second parameter is an inter-distance between differentiation reference points to be used for calculating a curvature value as the feature amount indicating the shape of the organ surface.

4. The image processing device recited in claim 1, wherein the parameter setting means further includes third parameter calculating means configured to calculate a third parameter based on the first parameter input by the parameter inputting means, and
wherein the lesion candidate detecting means further includes false-positive deleting means configured to determine a false-positive region by assessing a predetermined feature amount of the lesion candidate region extracted by the lesion candidate region extracting means using the third parameter calculated by the third parameter calculating means and deleting the lesion candidate region when the lesion candidate region is determined as the false-positive region.

5. The image processing device recited in claim 4, wherein the third parameter includes at least either a parameter indicating a size of the lesion candidate region or a parameter indicating a shape of the lesion candidate region.

6. The image processing device recited in claim 1, further comprising parameter correcting means configured to correct the parameter set by the parameter setting means in accordance with deformation of the medical image, wherein the lesion candidate region detecting means assesses the medical image using the parameter corrected by the parameter correcting means and detects the lesion candidate region based on a result of the assessment.

7. The image processing device recited in claim 6, wherein the medical image is a panoramic image displaying an inner surface of a hollow organ developed about an axis of the hollow organ.

8. The image processing device recited in claim 6, wherein the medical image is a virtual endoscope image obtained by projecting an inside of a hollow organ on a predetermined projection plane from a virtual point-of-view set in the inside of the hollow organ.

9. The image processing device recited in claim 1, further comprising a data table configured to preliminarily set values of the parameter in accordance with operating modes, wherein the parameter setting means includes first inputting means for reading out a value of the parameter corresponding to a selected operating mode from the data table and inputting the read-out value.

10. The image processing device recited in claim 1, further comprising second inputting means configured to input a numerical value as a value of the parameter, wherein the parameter setting means sets the numerical value input by the second inputting means as a value of the parameter.

11. The image processing device recited in claim 1, further comprising inputting means configured to display an object changing a size or shape thereof in accordance with a magnitude of a value of the parameter on a display screen displaying the medical image and inputting a value of the parameter through an operation with respect to the object, wherein the parameter setting means sets a value input by the inputting means in accordance with the size or shape of the object as a value of the parameter.

12. An image processing method of detecting a lesion candidate region from a medical image, comprising:
a parameter setting step of setting a parameter to be used for detecting the lesion candidate region; and
a lesion candidate region detecting step of assessing the medical image using the parameter set in the parameter setting step and detecting the lesion candidate region based on a result of the assessment,
wherein the parameter setting step further includes
inputting a first parameter indicating dimension of the lesion, and
calculating a second parameter based on the first parameter indicating the dimension of the lesion, and wherein the lesion candidate region detecting step further includes
- calculating a feature amount indicating a shape of an organ surface in the medical image, by using the second parameter, and
- extracting the lesion candidate region based on the feature amount calculated based on the second parameter which in turn was calculated based on the first parameter indicating the dimension of the lesion.

* * * * *